(12) United States Patent
Ott et al.

(10) Patent No.: US 11,788,669 B2
(45) Date of Patent: Oct. 17, 2023

(54) DEVICE FOR SUPPORTING AN IMAGE CAPTURING DEVICE ON A BIOREACTOR, BIOREACTOR WITH DEVICE FOR SUPPORTING AN IMAGE CAPTURING DEVICE, AND METHOD FOR PROPAGATION OR CULTIVATION OF BIOLOGICAL MATERIAL

(71) Applicant: SCHOTT AG, Mainz (DE)

(72) Inventors: Christian Ott, Ampfing (DE); Robert Hettler, Kumhausen (DE)

(73) Assignee: SCHOTT AG, Mainz (DE)

( * ) Notice: Subject to any disclaimer, the term of this patent is extended or adjusted under 35 U.S.C. 154(b) by 108 days.

(21) Appl. No.: 16/379,454

(22) Filed: Apr. 9, 2019

(65) Prior Publication Data
US 2019/0309253 A1 Oct. 10, 2019

(30) Foreign Application Priority Data
Apr. 9, 2018 (DE) ..................... 10 2018 108 323.8

(51) Int. Cl.
*F16M 11/00* (2006.01)
*C12M 1/00* (2006.01)
(Continued)

(52) U.S. Cl.
CPC ............ *F16M 11/00* (2013.01); *C12M 23/22* (2013.01); *C12M 23/48* (2013.01); *C12M 31/10* (2013.01);
(Continued)

(58) Field of Classification Search
CPC ....... F16M 11/00; C12M 23/22; C12M 23/48; C12M 31/10; C12M 37/04; C12M 41/46; C12M 43/00; C12M 41/06; G01N 21/255
See application file for complete search history.

(56) References Cited

U.S. PATENT DOCUMENTS

| 4,643,022 A | * | 2/1987 | Werlberger | ............ G01M 15/10 73/114.09 |
| 4,661,845 A | | 4/1987 | Saito | |

(Continued)

FOREIGN PATENT DOCUMENTS

| CN | 101526448 | 9/2009 |
| CN | 202022940 | 11/2011 |

(Continued)

OTHER PUBLICATIONS

Spier, "Application of Different Types of Bioreactors in Bioprocesses", Bioreactors: Design, Properties and Applications, 2011, pp. 55-90.
(Continued)

*Primary Examiner* — William H. Beisner
*Assistant Examiner* — Danielle B Henkel
(74) *Attorney, Agent, or Firm* — Ruggiero McAllister & McMahon LLC

(57) ABSTRACT

A supporting device for an image capturing device on a bioreactor, a bioreactor, and a method of use are provided. The supporting device for an image capturing device includes a window and a holder. The window has a transparent element that is transparent to electromagnetic radiation. The holder is configured to hold the image capturing device. The supporting device is held at least partially in a through-opening of a feedthrough of a container for holding fluid media containing biological material. The window seals the through-opening.

17 Claims, 9 Drawing Sheets

(51) Int. Cl.
*C12M 3/00* (2006.01)
*G01N 21/25* (2006.01)
*C12M 1/12* (2006.01)
*C12M 1/34* (2006.01)

(52) U.S. Cl.
CPC ............ *C12M 37/04* (2013.01); *C12M 41/46* (2013.01); *C12M 43/00* (2013.01); *G01N 21/255* (2013.01); *C12M 41/06* (2013.01)

(56) References Cited

U.S. PATENT DOCUMENTS

| | | | |
|---|---|---|---|
| 4,803,365 | A | 2/1989 | Krause |
| 5,709,724 | A | 1/1998 | Naugler |
| 5,866,910 | A | 2/1999 | Cooke |
| 7,491,668 | B2 | 2/2009 | Fechner |
| 8,183,035 | B1 | 5/2012 | Niazi |
| 8,809,037 | B2 | 8/2014 | Haley, III |
| 8,872,117 | B2 | 10/2014 | Lendl |
| 2001/0048525 | A1 | 12/2001 | Slater |
| 2003/0147132 | A1 | 8/2003 | Behnsen |
| 2003/0183001 | A1 | 10/2003 | Zimmermann |
| 2005/0135104 | A1 | 6/2005 | Crabb |
| 2007/0157748 | A1 | 7/2007 | Baumfalk |
| 2008/0003668 | A1 | 1/2008 | Uchiyama |
| 2008/0032389 | A1* | 2/2008 | Selker ............... C12M 23/00 435/283.1 |
| 2008/0171383 | A1* | 7/2008 | Selker ............... C12M 41/32 435/288.7 |
| 2009/0075362 | A1 | 3/2009 | Baumfalk |
| 2010/0035337 | A1* | 2/2010 | Bahnemann ......... C12M 41/36 435/292.1 |
| 2010/0190227 | A1 | 7/2010 | Dauth |
| 2010/0267125 | A1 | 10/2010 | Erb |
| 2010/0311156 | A1 | 12/2010 | Beliaev |
| 2012/0097557 | A1 | 4/2012 | Baumfalk |
| 2012/0152765 | A1 | 6/2012 | Trapp |
| 2012/0244609 | A1* | 9/2012 | Selker ............... C12M 29/06 435/295.1 |
| 2012/0288917 | A1 | 11/2012 | Krenbrink |
| 2012/0305946 | A1 | 12/2012 | Kuk |
| 2013/0039810 | A1 | 2/2013 | Riechers |
| 2013/0145818 | A1 | 6/2013 | Allgäuer |
| 2013/0171616 | A1 | 7/2013 | Niazi |
| 2013/0171723 | A1 | 7/2013 | Terentiev |
| 2013/0234274 | A1 | 9/2013 | Kam |
| 2014/0054186 | A1 | 2/2014 | Riechers |
| 2014/0071453 | A1 | 3/2014 | Riechers |
| 2014/0073035 | A1 | 3/2014 | Friederich |
| 2014/0209035 | A1 | 7/2014 | Tang |
| 2015/0330903 | A1* | 11/2015 | Koerperick ............ C12M 1/34 435/288.7 |
| 2015/0345689 | A1 | 12/2015 | Selker |
| 2016/0002580 | A1 | 1/2016 | Erickson |
| 2016/0083679 | A1 | 3/2016 | Johnson |
| 2016/0216154 | A1 | 7/2016 | Hofmeister |
| 2018/0372617 | A1* | 12/2018 | Hoehse ............... G01N 21/0303 |
| 2019/0017009 | A1* | 1/2019 | Yu ..................... C12M 41/44 |
| 2019/0309253 | A1 | 10/2019 | Ott |
| 2019/0309255 | A1 | 10/2019 | Ott |

FOREIGN PATENT DOCUMENTS

| | | |
|---|---|---|
| CN | 103517978 | 1/2014 |
| CN | 103710255 | 4/2014 |
| DE | 3446908 | 7/1985 |
| DE | 8703478 | 6/1987 |
| DE | 4416069 | 10/1995 |
| DE | 4423302 | 3/1996 |
| DE | 10016838 | 10/2001 |
| DE | 202006003878 | 6/2006 |
| DE | 102005035914 | 2/2007 |
| DE | 102006022307 | 11/2007 |
| DE | 102005012515 | 1/2008 |
| DE | 202008005412 | 7/2008 |
| DE | 102006001610 | 6/2009 |
| DE | 102009037345 | 12/2010 |
| DE | 102010014712 | 6/2011 |
| DE | 102010007559 | 8/2011 |
| DE | 102010012162 | 9/2011 |
| DE | 102010037923 | 4/2012 |
| DE | 102010063031 | 6/2012 |
| DE | 102011101107 | 11/2012 |
| DE | 102011101108 | 11/2012 |
| DE | 102011117228 | 5/2013 |
| DE | 102008036934 | 9/2014 |
| DE | 102013015106 | 3/2015 |
| DE | 202016000554 | 5/2017 |
| DE | 102016008826 | 1/2018 |
| DE | 102016215500 | 2/2018 |
| DE | 102018108323 | 7/2020 |
| DE | 102018108325 | 7/2020 |
| EP | 0456630 | 11/1991 |
| GB | 2469085 | 10/2010 |
| JP | H0484883 | 3/1992 |
| JP | 2002000256 | 1/2002 |
| JP | 2014527808 | 10/2014 |
| JP | 2015515270 | 5/2015 |
| WO | 2008145719 | 12/2008 |
| WO | 2009017721 | 2/2009 |
| WO | 2012016159 | 2/2012 |
| WO | 2012134820 | 10/2012 |
| WO | 2015142805 | 9/2015 |
| WO | 2015164274 | 10/2015 |
| WO | 2016167959 | 10/2016 |
| WO | 2017109104 | 6/2017 |
| WO | 2018014984 | 1/2018 |
| WO | 2018044748 | 3/2018 |
| WO | 2018129122 | 7/2018 |

OTHER PUBLICATIONS

Tosi, "Assessment of In-Line Near-Infrared Spectroscopy for Continuous Monitoring of Fermentation Processes", Biotechnol. Prog. 2003, vol. 19, No. 6, pp. 1816-1821.

Glaser, "Finding a Bioreactor That's Right For You", (https://www.genengnews.com/wn-content/uploads/2018/10/Sartorius_SSB_UniVessel6716630210.jpg) Aug. 1, 2011, 12 pages.

Bluma, "In-situ imaging sensors for bioprocess monitoring: state of the art", Anal. Bioanal. Chem., Springer, Sep. 12, 2010, 10 pages.

ASTM D 543-06, "Standard Practices for Evaluating the Resistance of Plastics to Chemical Reagents", Apr. 2, 2006, 7 pages.

DIN EN ISO 14937, "Sterilization of health care products—General requirements for characterization of a sterilizing agent and the development, validation and routine control of a sterilization process for medical devices", Mar. 2010, 50 pages.

EN ISO 17665-1, "Sterilization of health care products—Moist heat—Part 1: Requirements for the development, validation and routine control of a sterilization process for medical devices", Nov. 2006, 47 pages.

Kreis, "Adhesion of Chlamydomonas microalgae to surfaces is switchable by light", Nature Physics DOI: 10.1038/NPHYS4258, Sep. 25, 2017, 7 pages.

Ni, "Binding of phytochrome B to its nuclear signaling partner PIF3 is reversibly induced by light", (Phytochromes and gene expression), Nature 400, (1999), Abstract, 1 page.

Müller, "A red/far-red light-responsive bi-stable toggle switch to control gene expression in mammalian cells", Phytochromes and gene expression, Nucleic Acids Research, Published online Jan. 25, 2013, vol. 41 (7) :e77, 11 pages.

Adrian, "A Phytochrome-Derived Photoswitch for Intracellular Transport", DOI: 10.1021/acssynbio.6b00333, ACS Synthetic Biology, 6, 2017, pp. 1248-1256.

"SIMOTION—Description and example for the data exchange via OPC XML interface", Version 1.0 Edition Jul. 2007, published by Siemens AG, 33 pages.

ISO 10993-1, "Bilogical evaluation of medical devices—Part 1: Evaluation and testing within a risk management process", Fifth Edition, Aug. 2018, 48 pages.

(56) References Cited

OTHER PUBLICATIONS

Rudolph, "Entwicklung und Einsatz inline-mikroskopischer Verfahren zur Beobachtung biotechnologischer Prozesse", GottfriedWilhelm Leibniz Universitat Hannover, Nov. 5, 1977, 137 pages, with English Abstract.

Preacher, "Development of in-situ and flow microscopes for bioprocess technology", Hanover, 2013, English translation, 113 pages.

Rudolph, "Development and use of inline microscopic methods for observing biotechnological processes", Hanover, 2007, English translation, 161 pages.

English translation of SCHOTT web pages regarding BOROFLOAT, Apr. 9, 2021, 30 pages.

Inglish translation of SCHOTT BOROFLOAT product sheets, Apr. 9, 2021, 2 pages.

English translation of SCHOTT GTMS product sheets, Apr. 2012, 2 pages.

English translation of SCHOTT web pages regarding GTMS, Apr. 9, 2021, 2 pages.

Belini, "In Situ microscopy: A perspective for industrial bioethanol production monitoring", Journal of Microbiological Methods, vol. 93, 2013, pp. 224-232.

Boudoures, "A novel histone crosstalk pathway important for the regulation of UV-induced DNA damage repair in *Saccharomyces cerevisiae*" (2017) Genetics, 206 (3), Abstract, 6 pages.

Lee, "Inhibitory effects of ginsenosides on basic fibroblast growth factor-induced melanocyte proliferation", (2017) Journal of Ginseng Research, 41 (3), Abstract, 5 pages.

Zhang, "ROS and calcium signaling mediated pathways involved in stress responses of the marine microalgae Dunaliella salina to enhanced UV-B radiation", (2017) Journal of Photochemistry and Photobiology B: Biology, 173, Abstract, 6 pages.

Koller, "Model-supported phototrophic growth studies with Scenedesmus obtusiusculus in a flat-plate photobioreactor", (2017) Biotechnology and Bioengineering, 114 (2), Abstract, 6 pages.

Marose, "Optical sensor systems for bioprocess monitoring", TIBTECH Jan. 1999 (vol. 17), 7 pages.

ISO 2852, "Stainless steel clamp pipe couplings for the food industry", Second Edition, Jun. 15, 1993, 20 pages.

Huang, "UV-to-IR highly transparent ultrathin diamond nanofilms with intriguing performances: Anti-fogging, self-cleaning and self-lubricating", Applied Surface Science, vol. 527, 2020. DOI: https://doi.org/10.1016/j.apsusc.2020.146733. (Year: 2020).

English translation of WIKIPEDIA, "Laser welding", https //dc u ikipcdia orj:hi /indcx plipttltlc=Lascnielru ct "*C 5'ii9l-cn&ol, Dec. 12, 2022, 5 pages.

Rudolph, "Online Monitoring of Microcarrier Based Fibroblast Cultivations With In Situ Microscopy", Biotechnology and Bioengineering, vol. 99, No. i, Jan. 1, 2008, 12 pages.

Broadley James, "The Bioprocess Technologies Catalog", Broadley-James Corporation, Aug. 2014, 81 pages.

Xia, "The Fourth Round of Planning Textbooks for Pharmacy in National Colleges and Universities of Higher Education in Pharmacy", Jintong Higher Education "Eleventh Five-year Plan" (Yu Home Level Planning Textbook) with English translation.

\* cited by examiner

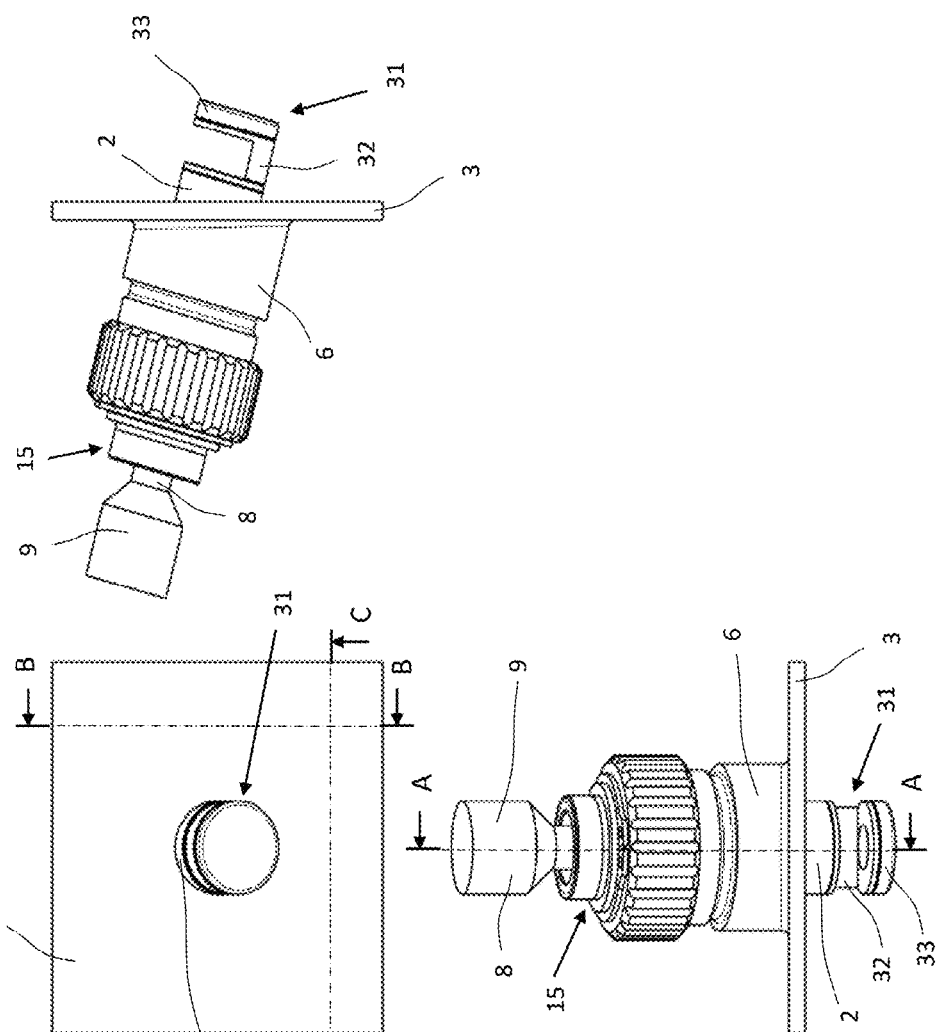
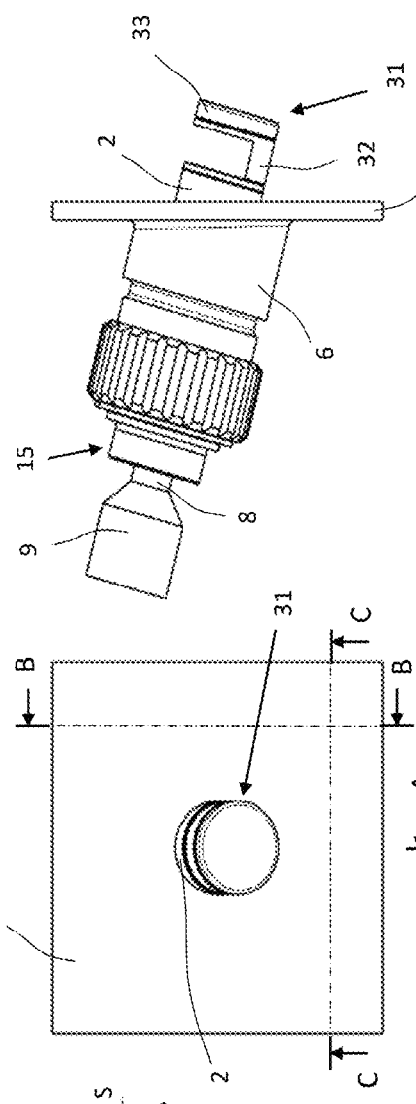
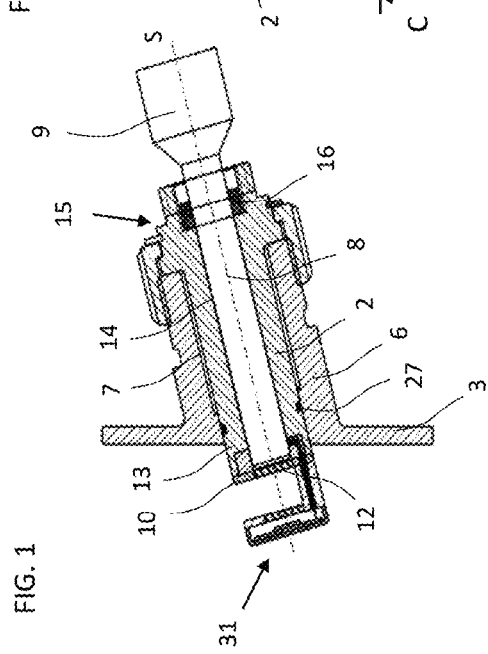

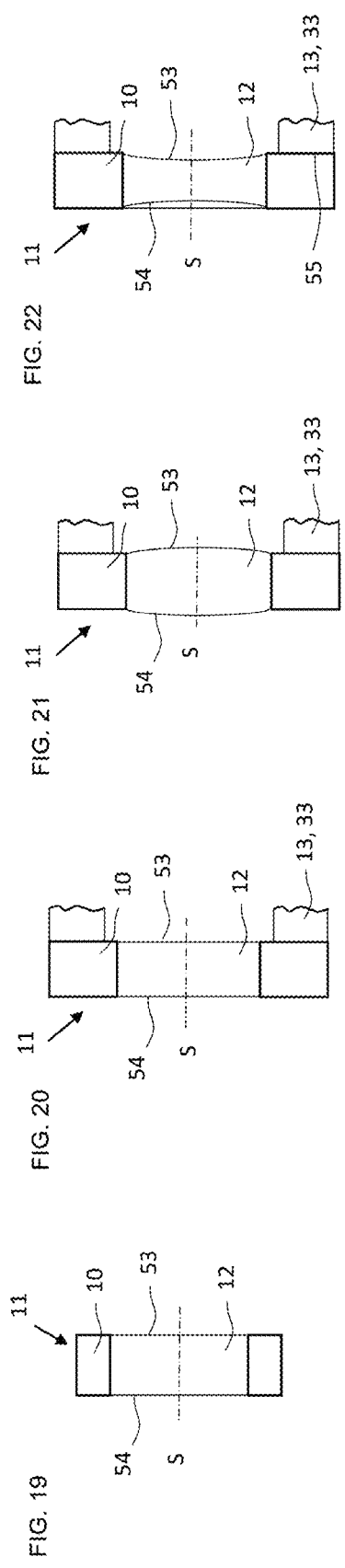
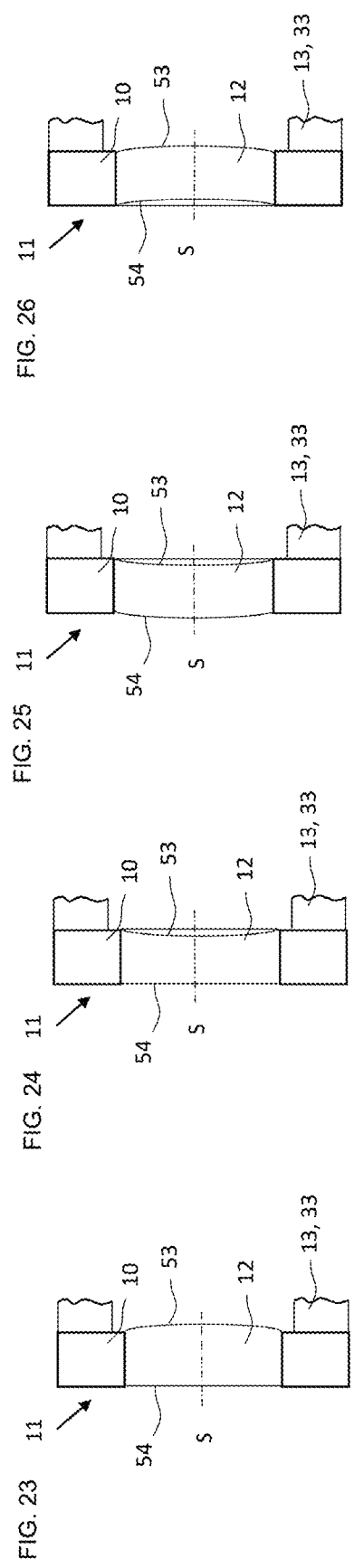

ents or the use of counting chambers. Turbidity measurement is usually performed by measuring the optical density. For this purpose, a sample, optionally diluted, is pipetted into a cuvette and is measured photometrically, for example at a wavelength of 880 nm. Drawbacks hereof are the increased risk of contamination due to the sample-taking and the unspecific measurement of all substances that absorb at the measured wavelength. For example, an increased extinction coefficient of lysed cells fatally suggests cell growth, even though the cells are actually in the dying phase. Also, infections are not detected in such measurements. The result may even be a total loss of the affected batch. For determining the actual vitality of the cells, a very time-consuming examination with a microscope and a slide with counting chamber has been performed hitherto. In addition, staining is often made, for example with Trypan blue. Although the
DEVICE FOR SUPPORTING AN IMAGE CAPTURING DEVICE ON A BIOREACTOR, BIOREACTOR WITH DEVICE FOR SUPPORTING AN IMAGE CAPTURING DEVICE, AND METHOD FOR PROPAGATION OR CULTIVATION OF BIOLOGICAL MATERIAL

CROSS REFERENCE TO RELATED APPLICATIONS

This application claims benefit under 35 USC § 119 of German Application 10 2018 323.8, filed Apr. 9, 2018, the entire content of which are incorporated herein by reference.

The present application incorporates by reference the entire content of U.S. application Ser. No. 16/379,133 filed simultaneously with the present application and the entire content of German Application 10 2018 108 325.4 filed Apr. 9, 2018 on which it is based.

The present application incorporates by reference the entire content of U.S. application Ser. No. 16/379,161 filed simultaneously with the present application and the entire content of German Application 10 2018 108 327.0 filed Apr. 9, 2018 on which it is based.

BACKGROUND

1. Field of the Invention

The invention relates to a device for supporting an image capturing device on a bioreactor and to a bioreactor including a device for supporting an image capturing device.

2. Related Art

Methods and device for producing biological material, such as for example biotechnological production processes involving the cultivation of microorganisms, animal and plant cells, are of increasing importance. Biotechnological production processes include, for example, the cultivation of microorganisms, animal and plant cells. What is crucial for the development and control of biotechnological production processes, however, is the monitoring of cell growth and of the vitality of cells within the bioreactor. This has an impact on the product yield and thus on the profitability of the entire process.

Conventionally, for determining cell growth and the vitality of the cells, samples are usually taken from the bioreactor and are then analyzed outside the bioreactor, or off-line. However, this provides no real-time process control. Standard procedures in this context include turbidity measurements or the use of counting chambers. Turbidity measurement is usually performed by measuring the optical density. For this purpose, a sample, optionally diluted, is pipetted into a cuvette and is measured photometrically, for example at a wavelength of 880 nm. Drawbacks hereof are the increased risk of contamination due to the sample-taking and the unspecific measurement of all substances that absorb at the measured wavelength. For example, an increased extinction coefficient of lysed cells fatally suggests cell growth, even though the cells are actually in the dying phase. Also, infections are not detected in such measurements. The result may even be a total loss of the affected batch. For determining the actual vitality of the cells, a very time-consuming examination with a microscope and a slide with counting chamber has been performed hitherto. In addition, staining is often made, for example with Trypan blue. Although the resulting time expenditure can be countered with cost-intensive instrumental analytics, such as a flow cytometer or Coulter counter, the increased risk of contamination and the lack of determination in real time remain disadvantageous.

Although data from the interior of the bioreactor can be provided by sterilizable turbidity probes, these also exhibit the drawbacks of a turbidity measurement, as described above, due to the measuring method.

DE 10 2010 063 031 A1 discloses a potentiometric sensor and a method for starting up a potentiometric sensor. In order to particularly simplify the use of a container serving as a single-use fermenter or single-use bioreactor, the potentiometric probe disclosed therein can be installed in a wall of the container, via a port, already before sterilization, for example by irradiation with gamma radiation, and can remain therein for the duration of storage and use.

Document DE 10 2006 022 307 A1 describes a one-way bioreactor comprising a reversibly externally attachable sensor arrangement for measuring a physical variable of a contained medium, and a sensor adapter for receiving an electronic sensor arrangement that is interacting with the medium flowing through the peripheral line, via an inner interface of the sensor adapter, is integrated in at least one peripheral line of the bioreactor serving for the inlet and/or outflow of medium. Since the measurement can be made only in the peripheral line of the bioreactor, process control within the bioreactor is impossible with this arrangement.

DE 10 2010 037 923 A1 discloses a bioreactor arrangement for cells, comprising a closed bioreactor, a cell pellet carrier for receiving a cell pellet, and means for supplying nutrient solution into the cell pellet. This arrangement allows for contactless measurement of the oxygen content. For this purpose, oxygen probes are excited to phosphorescence by a laser. The emitted phosphorescence signal is captured by the detector and fed to evaluation electronics. For this purpose, the bioreactor has light-transmitting windows, and the laser and the detector are arranged outside the bioreactor. An exchange of sensors or measuring equipment is not described in this document.

DE 10 2011 101 108 A1 describes a transflection probe for performing a transflection measurement on a fluid located in a rigid container, comprising a probe shaft having a light guide path in the interior thereof, and having an open flow chamber on the front end face, with a reflective plate arranged opposite the front end face of the probe shaft. The probe shaft is in the form of a rigid chamber which is sealed at its front end face by a transparent window and which has a first coupling device at its rear end for rigidly coupling a sensor module to the probe shaft. However, this coupling device is firmly connected to the open flow chamber and in particular to the reflective plate arranged opposite the front end face of the probe shaft, so that an exchange of sensor modules on a probe or the coupling of a sensor module to different probes of the same or of a different container in an alternating manner is possible. An exchange of sensors for measuring physical, chemical, or biological parameters is not disclosed.

DE 10 2011 117 228 A1 relates to a microscopy system for determining the condition of biological cells, which comprises an optical image capturing unit with an optical sensor and an optional illumination unit. The optical image capturing unit is enclosed by a water- and moisture-tight casing that is formed by an optically transparent layer over a sensor surface of the optical sensor or at least one region of this sensor surface. The transmission of captured image data of cells that adhere to the optically transparent layer to an external receiver unit allows the microscopy system to be used for determining the condition of cells directly in a bioreactor. The microscopy system consists of an extremely miniaturized microscope, a wireless data transfer unit, a power supply unit, a suitable water- and moisture-tight and sterilizable housing and a receiver unit located outside the bioreactor. A drawback of this microscopy system is that the microscope is disposed within the medium to be examined, which limits the operating time because of the necessary power supply, since a CCD chip is used for image capturing, which is used as a miniaturized image capturing and imaging unit. Moreover, during a production process, for example, an intervention on this microscope and an exchange thereof is not possible. Since a CCD chip is employed, the optical resolution of this microscope is limited by the pixel size of the photosensors of the chip.

SUMMARY

The invention is based on the object of configuring image capturing systems and preferably imaging systems in such a way that they can be mounted to a bioreactor in an exchangeable manner while being capable of at least capturing image data of a volume located within the bioreactor, but preferably also of processing such image data for imaging purposes or transferring such image data.

For the purposes of the present disclosure, the capturing of image information, in particular by image capturing devices or systems, refers to the capturing of fields of electromagnetic waves, in particular fields of waves within the container of a bioreactor in a spectral range of wavelengths from 250 to 2000 nm in an optical device, in particular in a microscopic device such as a microscope, or else the capturing of fields of electromagnetic waves, in particular in a spectral range of wavelengths from 250 to 2000 nm in electro-optical devices, such as in individual photosensors or in photosensors arranged in an array, such as CCD or CMOS sensors comprising either a linear array or a 2-dimensional array of photosensors, which are also referred to as pixels in the context of this disclosure. These electro-optical devices may form part of an optical system or may else directly capture the respective field of electromagnetic waves. The respective field of waves may be consistent over time or may be present in the form of bursts, i.e. time-limited pulses or light pulses, which then are also referred to as stroboscopically emitted fields of waves, which are present and can be detected in a chronologically defined sequence.

Processing for imaging purposes herein refers to both, the influencing of optical beam paths, as is the case in microscopic devices, for example, and the conversion of electrical signals, in particular opto-electrical signals into a data format that includes image data, in particular also digital image data.

Preferably, the distance of the fluid medium in the bioreactor to the image capturing unit, in particular to a microscopic device, shall have only a minor impact on the optical capturing, or the device according to the invention may even constitute a beam-forming portion of an image capturing device in preferred embodiments.

In contrast to the prior art, the invention provides effective in-situ process control. In the production of biopharmaceuticals, for example, this provides for a lower production risk and a higher yield during continuous operation without having to interrupt a cost-intensive production process due to a lack in power supply.

Compared to the prior art, the preferred embodiments have the further advantage that the distance between an image capturing unit and fluid medium, in particular also the biological material contained therein, can be altered variably and flexibly, even during the cultivation. The complete optical unit and also the image capturing unit including the number and distance of all optical lenses and contrast systems can be exchanged flexibly at any time without an additional risk of contamination.

Due to the mechanical separation of the assembly to be sterilized from the microscopic device, it is possible to satisfy requirements for sterility on the one hand and for the choice of material of the microscopic device on the other hand more efficiently and independently of each other. For example, with the invention, the material requirements for sterilization and possible restrictions on admission are eliminated, also for conventional microscope probes, which translates not only into constructive, but also into cost benefits.

The sterile area within the container for holding fluid media containing biological material of the respective bioreactor is separated from the area outside the bioreactor, while microscopic devices such as microscope probes can be held in a mechanically stable manner. The invention is applicable both to one-way bioreactors, also known as single-use reactors, as well as to bioreactors intended for repeated use, which are commonly referred to as multi-use reactors in the art.

A bioreactor according to the invention comprises a container for holding fluid media containing biological material, a feedthrough with a through-opening between the interior of the container for holding fluid media containing biological material and the exterior of the container for holding fluid media containing biological material, a device for supporting an image capturing device, in particular a microscopic device, which has a window including a transparent element that is transparent to electromagnetic radiation and a holder for the image capturing device, wherein the device for supporting an image capturing device is held at least partially in the through-opening of the feedthrough, while the window seals the through-opening. Here, the wording that the window seals the through-opening is meant to include that the device for supporting an image capturing device in combination with its window seals the through-opening.

Preferably, the feedthrough comprises a standard port, such as an Ingold port, a Broadly James port, a B. Braun safety port, or a port in compliance with a different standard. In one-way reactors or single-use reactors, the feedthrough may also comprise a tri-clamp port, sanitary clamp port, or a manufacturer-specific, in particular manufacturer-specifically adapted port.

In particular in the case of a single-use reactor, fastening with external fastening means, such as a snap lock, may additionally be provided.

Such ports each have a through-opening of a defined diameter, which typically connects the interior of a bioreactor to the exterior thereof or opens to the exterior.

Generally, the container for holding fluid media containing biological material may be the container of a multi-use bioreactor intended for repeated use.

Advantageously in this case, the container for holding fluid media containing biological material comprises stainless steel or is made of stainless steel. The device for supporting an image capturing device on a bioreactor may also comprise stainless steel, or at least one or more of its components and the main body of the windows disclosed herein may be made of stainless steel.

Any stainless steels may be used, especially also austenitic and ferritic stainless steels, but preferably only as far as they remain rust-free when practicing the invention.

The stainless steel may preferably also comprise or entirely consist of 316L pharmaceutical grade steel.

Furthermore, titanium, tantalum, niobium, alloys thereof, and Monel alloy with a high copper content may also be used, in principle, and when the material is used for the illumination device which is a device for emitting electromagnetic radiation, in particular for the housing body thereof, it may also be enameled.

Alternatively, the container for holding fluid media containing biological material may also be the container of a single-use bioreactor intended for one-way use.

In this case, it is advantageous if the container for holding fluid media containing biological material comprises a plastic, in particular a sterilizable plastic, or is made of a plastic, in particular a sterilizable plastic. This plastic may comprise a polymeric material and may in particular be made of a suitable material which withstands gamma sterilization or chemical sterilization with ETO.

In order to meet the stringent requirements for the production of biopharmaceuticals, the material of the bioreactor and of the sensor receptacle may each be selected so as to comply with the following standards: FDA approved materials (ICH Q7A, CFR 211.65(a) —Code of Federal Regulations, USP Class, animal derivative free, bisphenol A free); EMA (European Medicines Agency) EU GMP Guide Part II approved materials; Sectoral chemical resistance—ASTM D 543-06; and Biocompatibility, e.g. referred to US Pharmacopeia or tests referred to ISO 10993.

It is particularly advantageous if the bioreactor is autoclavable together with the device for supporting an image capturing device, in particular autoclavable while the latter is held at least partially in the through-opening of the feedthrough, because this permits to exclude with a very high degree of certainty a contamination with biologically active or interacting material.

For this purpose, the device for supporting an image capturing device is in particular adapted to be autoclavable as well.

Surprisingly, it has been found that 3,500 autoclaving cycles at 2 bar and 134° C. were possible with the devices for supporting an image capturing device as disclosed herein.

In the context of this disclosure, autoclavable is understood to mean autoclavable in the sense of DIN EN ISO 14937; EN ISO 17665, which applies to medical devices.

With a window including a transparent element that is transparent to electromagnetic radiation and a holder for an image capturing device it is possible to reliably protect the sterile area, even if image capturing or imaging devices should be exchanged during a production process.

A mechanically stable assembly is obtained with a main body to which the transparent element of the window is secured in a hermetically sealed manner, preferably by a compression glass seal, in particular a glass-to-metal seal GTMS compression glass seal.

Mechanical stability is further promoted if a holder body of the device for supporting an image capturing device has a cylindrically symmetrical shape, in particular a columnar shape, and has a through-opening which is sealed fluid-tightly, in particular hermetically by the window on the side associated with the interior of the bioreactor. Since this allows a microscopic device to even come into direct contact with the transparent element of the window, high numerical apertures are made possible for imaging systems, which can provide a far better optical imaging performance than was hitherto possible.

Advantageously, the transparent element of the window exhibits a transmittance of greater than 80%, most preferably greater than 90%, in a spectral range of wavelengths between 250 and 2000 nm.

In a particularly preferred embodiment, the transparent element of the window comprises glass or is made of glass.

Preferably, the glass of the transparent element of the window may comprise quartz glass or borosilicate glass.

Optical advantages may result for image capturing and imaging systems when the transparent element of the window has a sheet-like shape and in particular plane-parallel main surfaces. For example, in microscope optics it is in particular known for the use of plane-parallel cover plates to correct plane-parallel optical beam interferences and thereby still achieve maximum optical performance. Such optical corrections can also be used in this preferred embodiment, in particular with an advantageously improved distortion-free design.

If, however, the transparent element of the window is one of plano-convex, plano-concave, biconvex, biconcave, convexo-concave, or concavo-convex, it may even itself form part of an imaging system.

In this case, the transparent element of the window may preferably form part of a microscopic device associated therewith.

The holder body may have a radially extending lateral shoulder, in particular in order to provide a stop in the axial direction for a standard port on the bioreactor.

In this case, when the device for supporting an image capturing device is installed in the through-opening, the axial distance between the transparent element of the window and the inner surface of the bioreactor can be defined by the axial distance of the transparent element of the window to the lateral shoulder. In this case, when the holder body is installed in the through-opening, in particular when the lateral shoulder abuts on a standard port, the transparent element of the window is advantageously arranged within the bioreactor. A set of holder bodies with different axial distances between the transparent element of the window and the lateral shoulder may thereby allow for a selectable axial arrangement of the transparent element of the window within the bioreactor. In the context of the present disclosure, axial distance is understood to mean a distance measured or indicated in the direction of the axis of symmetry of the cylindrically symmetrical holder body of the sensor receptacle.

Very advantageous is an illumination device, which is disposed on the holder body, preferably in a detachably mountable manner, on the side associated with the interior of the container for holding fluid media, because it allows to provide defined lighting conditions for the fluid medium or the fluid media to be subsequently captured by the image capturing device, in particular microscopic device.

Preferably, the illumination device comprises a housing and further window, preferably comprising a further main body and a further transparent element, which in its mounted state is arranged opposite the window of the device for supporting an imaging device. In this way, a defined illumination field is provided which allows for defined image capturing.

In the sense of the present disclosure, mounted state refers to the state in which the illumination device is mounted, preferably detachably mounted, to the holder body and assumes its operating position, as will be described in more detail below.

Further advantages are moreover obtained if the transparent element of the window, which is disposed on the holder body of the device for supporting an image capturing device is attached to the main body by a compression glass seal, in particular a GTMS compression glass seal, and the main body is preferably attached to the holder body by a welded connection, and/or if the transparent element of the window of the illumination device is attached to the main body by a compression glass seal, in particular a GTMS compression glass seal, and the main body is attached to the housing of the illumination device by a welded connection, since in this case a mechanically and thermally stable connection is provided which even withstands autoclaving, in a durable and safe manner, as well as cleaning and sterilization using procedures that are known as CIP (Clean-In-Place) and SIP (Sterilization-In-Place).

The microscope-side transparent element of the window on the main body, in particular of the glass-to-metal seal (GTMS) window, is preferably ground and polished after the compression glass seal has been established. This allows for particularly distortion-free image capturing and imaging.

The transparent element of the window on the side of the illumination device, in particular of the GTMS window, allows for optimized illumination for the respective image capturing process.

Particularly preferably, the main body of the window of the device for supporting an image capturing device is connected to the holder body in a hermetically sealed manner, by a welded connection, in particular by welding, in particular laser welding, and optionally the main body of the window of the illumination device is connected to the housing of the illumination device in a hermetically sealed manner as well, by a welded connection, in particular by welding, in particular by laser welding.

For the purposes of the present disclosure, GTMS compression glass seal is understood to mean a compression glass seal between a glass sheet, in particular a respective transparent element, and a metal surrounding it, which is known per se to a person skilled in the art. In this case, a circular sheet may be arranged within a metal ring, to which it is fused at elevated temperature and is kept fluid-tight and in particular hermetically sealed under pressure by a subsequent temperature reduction.

Generally, it is advantageously possible to establish a further fluid-tight and hermetically sealed connection by welding, in particular laser welding, in particular after the compression glass seal has been established, for example between the main body of the compression glass sealed window and the holder body, or between the main body of the compression glass seal of the further window and the housing of an illumination device.

Advantageously, in their mounted state within the container for holding fluid media, the device for supporting an image capturing device and its illumination device may define a chamber with a defined volume that is open in particular towards at least two sides perpendicular to the symmetry axis of the holder body. In this way, a defined measuring chamber can be provided within the container for holding fluid media, which also allows to perform turbidity measurements under defined boundary conditions and in real time. Such measurements may in particular be performed alternatively or in parallel to the respective image capturing. For this purpose, it is moreover possible to evaluate image data which have been forwarded from the image capturing device to an imaging device.

In this case, or more generally in all embodiments, the transparent element of the window of the illumination device and the transparent element of the window which is arranged on the holder body of the device for supporting an imaging device may advantageously have a predefined spacing from each other.

In a particularly preferred embodiment, the device for supporting an image capturing device may comprise at least one electrical connector on the holder body thereof, and the illumination device may likewise comprise an electrical connector on the housing thereof, which electrical connectors are each hermetically sealed and are complementary interengagable, thereby preferably allowing to control the illumination device from externally of the bioreactor. In a preferred embodiment, this hermetic sealing, in particular in a plug-in version, comprises a housing of a respective plug which is sealed to the holder body or to a base part by a respective elastomeric component. Approved materials for this purpose include EPDM, NBR, or FKM, for example.

Alternatively or additionally, the device for supporting an image capturing device may comprise at least one inductive coupler on the holder body thereof, and the illumination device may comprise at least one inductive coupler on the housing thereof, which inductive couplers are adapted to be coupled inductively in their mounted state and are each hermetically sealed.

In the sense of the present disclosure, an item or else a connection between two items, for example between the transparent element 12 and the main body 10 of the window 11, shall be considered as hermetically sealed or fluid-tight if it exhibits a leak rate of less than $1*10^{-3}$ mbar·l/sec at room temperature when exposed to He on one side and to a pressure difference of 1 bar.

Preferably, the illumination device comprises an LED or an array of LEDs arranged in the housing of the illumination device in each case.

In a particularly preferred embodiment, the LEDs, which may also be OLEDs, can be driven stroboscopically by an associated electronic unit, in particular a process control device (PST), in particular also in order to mitigate blurring caused by movements of the biological material within the fluid medium or fluid media or to even avoid such blurring with appropriately short light-emitting pulses or bursts.

In this way it is even possible to capture sharp, automatically evaluable images of the fluid medium, in particular of a cell suspension which is in motion due to the stirring element.

The triggering of an LED flash or burst in a clocked manner and in synchronism with a respective image capturing will be advantageous in this case.

In the context of the present disclosure, the terms light and electromagnetic radiation are used synonymously. However, the term 'electromagnetic radiation' is used in order to include in the disclosure that the present invention is not limited to the spectral range of visible light, as can also be seen from the transmission properties of the glasses disclosed herein, for example.

Furthermore, in the case of stroboscopic illumination, the light may be emitted in a time-synchronous or time-asynchronous manner, with the term 'synchronous emission of light' referring to synchronous image capturing by the microscopic device. Synchronous image capturing can be used to reduce blurring, and asynchronous emission of electromagnetic radiation, for example with subsequent image capturing with a time-offset, can be used to capture an "afterglow" of the biological material or of the fluid medium, for example, which is useful for monitoring metabolic processes of the biological material.

Preferably, the invention furthermore comprises a method for propagation or cultivation of biological material, comprising the introducing of fluid media containing biological material or of a precursor of biological material into a bioreactor in particular as disclosed above, in particular into a container of the bioreactor for holding fluid media containing biological material, wherein the container for holding fluid media containing biological material has a feedthrough with a through-opening between the interior of the container for holding fluid media containing biological material and the exterior of the container for holding fluid media containing biological material, and comprising, prior to the introducing of the fluid media containing biological material or a precursor of biological material, the mounting, at or in the through-opening of the feedthrough of the container for holding fluid media containing biological material, of a device for supporting an image capturing device, in particular a microscopic device, which comprises a window including a transparent element that is transparent to electromagnetic radiation, and a holder for the image capturing device.

Particularly preferably, the method for propagation or cultivation may comprise the production of pharmaceuticals, in particular of biopharmaceuticals. Here, the term 'cultivation' also encompasses the preparation of the biological material, which also means an alteration and even a damage thereof, for example because increased yields in the propagation of biological material can be achieved through cellular repair mechanisms.

A particular advantage is obtained if the bioreactor is sterilized after the device for supporting an image capturing device, in particular a microscopic device, has been mounted, since in this case it is possible to always provide a sterile bioreactor and to reduce the risk of contamination, independently of an image capturing device disposed in the device for supporting an image capturing device, and also independently of an exchange of a device arranged in the device for supporting an image capturing device.

After the mounting of the device for supporting an image capturing device, it may advantageously be equipped with an image capturing device and the capturing of image information using the image capturing device can be performed.

Particularly advantageously, electromagnetic radiation can be emitted, in particular irradiated into the container for holding fluid media, by an illumination device which is preferably disposed on the holder body, preferably in a detachably mountable manner, on the side associated with the interior of the container for holding fluid media.

In this case, in a preferred embodiment, the illumination device may emit electromagnetic radiation in the form of time-limited pulses.

The time-limited pulses may, for example, have a duration per pulse of 1 ms to less than one thousandth of a microsecond.

The time-limited pulses of the electromagnetic radiation may be emitted in a time-synchronous manner and thus at fixed time intervals, or else in a time-asynchronous manner and thus at varying time intervals.

If the time-limited pulses of the electromagnetic radiation are emitted in a time-synchronous manner, this means in the sense of the present disclosure that these pulses are preferably emitted at a fixed frequency.

Such fixed frequencies may range from one Hz to several MHz, especially when laser LEDs are used for emitting the time-limited pulses.

Particularly advantageously, the capturing of image information using the image capturing device may be performed during a time-limited interval in synchronism with the emission of electromagnetic radiation in the form of time-limited pulses.

In a further particularly preferred embodiment, the device for supporting an image capturing device comprises at least one sensor, and in the operating state it is possible to measure the radiation intensity and/or wavelength of the electromagnetic radiation in the interior of the bioreactor.

Particularly preferably in this case, the radiation intensity and/or wavelength of the electromagnetic radiation in the interior of the bioreactor can be measured in a spatially resolved manner during the operating state, for example using an image capturing device such as a microscope probe.

If electromagnetic radiation of a defined wavelength, preferably 250 nm, is irradiated into the bioreactor for a defined period of time, and a radiation intensity and/or a wavelength of the electromagnetic radiation is measured inside the bioreactor over a broad range of wavelengths or selectively at a particular wavelength, in particular at 270 nm, this allows to detect portions of the light emitted due to fluorescence and to evaluate them with regard to defined metabolic processes within the bioreactor.

Particularly preferably, the methods described herein use photo- or mixotrophic microorganisms modified by mutagenesis, in particular microalgae, yeasts, and bacteria.

The invention and its preferred embodiments permit to achieve a mitigation in the risk of contamination, since in particular no samples need to be extracted anymore, and since production control can be done in real time. During cultivation, the user can safely change the image capturing device, for example a microscope probe, and there is no longer any loss of control in the event it is defective. Monitoring of cell growth including the identification of morphology, the identification of vital and proliferating cells, the identification of fragments of lysed cells and of infections and contaminations is made possible on a permanent basis, which promotes increases in yield.

Very advantageous is a method in which the bioreactor is autoclaved together with its container for holding fluid media containing biological material and with the device for supporting an image capturing device while the device for supporting an image capturing device is held at least partially in the through-opening of the feedthrough and, preferably, while the window seals the through-opening, because in this case contamination of the bioreactor can be avoided with much higher probability than hitherto, and the autoclaving can be performed with a single operation. Consequently, if the autoclaving is carried out shortly before the bioreactor is filled with the biological material, the risk of an interim introduction of contaminants is also reduced.

With the methods presently disclosed it is possible to use in particular photo- or mixotrophic microorganisms modified by mutagenesis, in particular also microalgae, yeasts, and bacteria.

The embodiments described herein, in particular also the embodiments of the method allow to identify processes within a bioreactor in a very flexible way and with high precision.

The article "Adhesion of *Chlamydomonas* microalgae to surfaces is switchable by light", by Christian Titus Kreis, Marine Le Blay, Christine Linne, Marcin Michal Makowski, and Oliver Baumchen, NATURE PHYSICS DOI: 10.1038/

NPHYS4258 describes the behavior of microalgae which could be caused to adhere to or detach from surfaces in response to irradiation of light. By selective irradiation of electromagnetic radiation of appropriate wavelength it is now possible to achieve, for example in photobioreactors which are used in repeated batch operation, that during the change of a medium, such as nutrient solution, these microalgae adhere to surfaces and re-detach from the surface after the medium has been supplied. This also allows to further increase the effectiveness of the operation of photo-bioreactors. Such behavior of microalgae can be monitored with the image capturing devices described herein, for example.

In their publication (Phytochromes and gene expression), "Binding of phytochrome B to its nuclear signaling partner PIF3 is reversibly induced by light", Nature 400, 781-784, the authors Ni, M., Tepperman, J. M., and Quail, P. H. (1999) describe that gene expression can be specifically induced by light, via the respective cell signaling pathways.

The publication "A red/far-red light-responsive bi-stable toggle switch to control gene expression in mammalian cells", by Konrad Müller, Raphael Engesser, Stephanie Metzger, Simon Schulz, Michael M. Kämpf, Moritz Busacker, Thorsten Steinberg, Pascal Tomakidi, Martin Ehrbar, Ferenc Nagy, Jens Timmer, Matias D. Zubriggen, and Wilfried Weber, Nucleic Acids Research, 2013 April; 41(7): e77, describes this mechanism for mammalian cells for controlling transgenic activity.

Optogenetic control is also described in "A Phytochrome-Derived Photoswitch for Intracellular Transport", by Max Adrian, Wilco Nijenhuis, Rein I. Hoogstraaten, Jelmer Willems, and Lukas C. Kapitein, DOI: 10.1021/acssynbio.6b00333, ACS Synth. Biol. 2017 Jul. 21; 6(7): 1248-1256. According to this document, intracellular bi-directional transport mechanisms can be controlled in a wavelength-specific manner. Here, a process control using image capturing devices is extremely helpful, also as a signal for feedback to the process controller.

BRIEF DESCRIPTION OF THE DRAWINGS

The invention will be described in more detail below by way of preferred embodiments and with reference to the following drawings, wherein FIG. 1 is a cross-sectional view of a first preferred embodiment of a device for supporting an image capturing device which is arranged in a through-opening of a container for holding fluid media containing biological material, although the container is shown only partially, the view being taken along a sectional plane illustrated as sectional plane A-A in FIG. 4;

FIG. 2 is a view obliquely from above, but as seen from the interior of a container for holding fluid media, of the first preferred embodiment of the device for supporting an image capturing device which is arranged in a through-opening of the container for holding fluid media containing biological material, although the container is shown only partially;

FIG. 3 is a cross-sectional view of the first preferred embodiment of the device for supporting an image capturing device which is arranged in a through-opening of a container for holding fluid media containing biological material, although the container is shown only partially, the view being taken along a sectional plane illustrated as sectional plane B-B in FIG. 2;

FIG. 4 is a cross-sectional view of the first preferred embodiment of the device for supporting an image capturing device which is arranged in a through-opening of a container for holding fluid media containing biological material, although the container is shown only partially, the view being taken along a sectional plane illustrated as sectional plane C-C in FIG. 2;

FIG. 19 is a schematic sectional view along an axis of symmetry S of a window described herein for explaining the method of producing such window;

FIG. 20 is a schematic sectional view taken along the axis of symmetry S of a window of the device for supporting an image capturing device, showing part of the holder body of the device for supporting an image capturing device and a plane-parallel transparent element;

FIG. 21 is a schematic sectional view taken along the axis of symmetry S of a window of the device for supporting an image capturing device, showing part of the holder body of the device for supporting an image capturing device and a biconvex transparent element;

FIG. 22 is a schematic sectional view taken along the axis of symmetry S of a window of the device for supporting an image capturing device, showing part of the holder body of the device for supporting an image capturing device and a biconcave transparent element;

FIG. 23 is a schematic sectional view taken along the axis of symmetry S of a window of the device for supporting an image capturing device, showing part of the holder body of the device for supporting an image capturing device and a plano-convex transparent element;

FIG. 24 is a schematic sectional view taken along the axis of symmetry S of a window of the device for supporting an image capturing device, showing part of the holder body of the device for supporting an image capturing device and a plano-concave transparent element;

FIG. 25 is a schematic sectional view taken along the axis of symmetry S of a window of the device for supporting an image capturing device, showing part of the holder body of the device for supporting an image capturing device and a convexo-concave transparent element;

FIG. 26 is a schematic sectional view taken along the axis of symmetry S of a window of the device for supporting an image capturing device, showing part of the holder body of the device for supporting an image capturing device and a concavo-convex transparent element;

DETAILED DESCRIPTION

Figure 6:
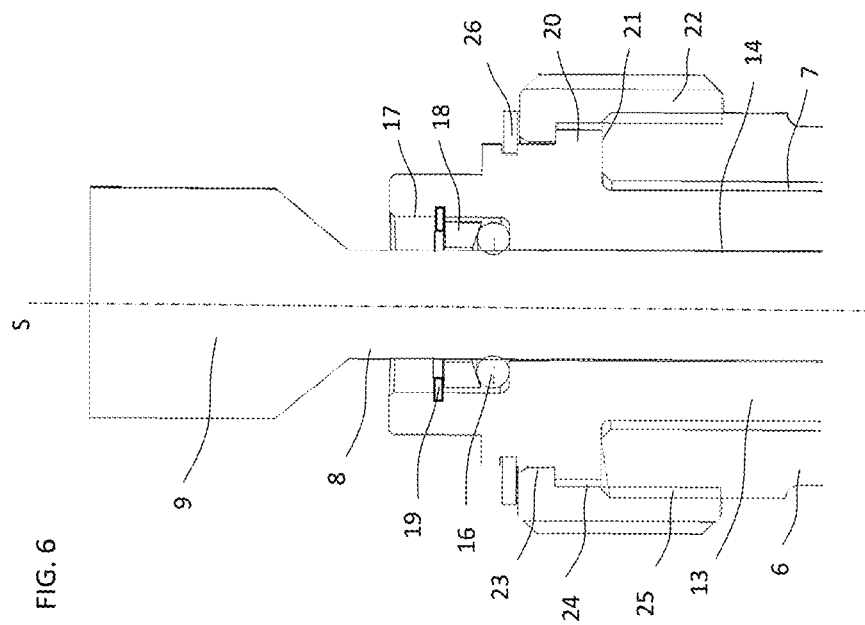
FIG. 6 is a detail view of an upper portion of FIG. 5.

In the following detailed description of preferred embodiments, the same or equivalent components in the figures are designated with the same reference numerals in each case.

However, the figures are not drawn to scale, for the sake of clarity.

For the sake of brevity, the container for holding fluid media containing biological material will also be referred to as a container for holding fluid media hereinafter, or else, even more briefly, only as a container.

Insofar as the term 'fluid media' is used in the context of the present disclosure, this takes account of the fact that more than one fluid constituent may be provided in a bioreactor, for example a carrier fluid which may contain the biological material or a precursor of the biological material, but which may also include fluid components of the biological material itself or further nutrient solution. However, if there is only one carrier fluid and no other fluid component contained in the bioreactor, the term 'fluid media' is meant to encompass this carrier fluid also in the singular, without the need of additionally having further fluid constituents.

In the context of the present disclosure, the biological material generally comprises prokaryotic and eukaryotic cell cultures, such as mammalian cells, photo-, hetero-, and mixotrophic microorganisms, and is for instance provided in the form of microalgae, for example blue-green algae or cyanobacteria, and in particular also comprises photo- or mixotrophic microorganisms that have been modified by mutagenesis, in particular also yeasts, and bacteria.

Figure 12:
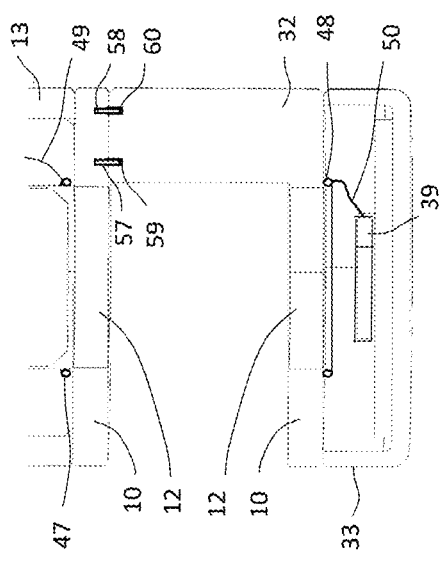
FIG. 12 is a side view of a bioreactor with a device for supporting an image capturing device, showing the container for holding fluid media containing biological material partially broken away.

Referring first to FIG. 12 which shows a multi-use bioreactor designated by reference numeral 1 as a whole, which has disposed thereon a device for supporting an image capturing device, designated by reference numeral 2 as a whole.

The bioreactor 1 comprises a container 3 for holding fluid media that contains biological material, and both the fluid medium 4 or fluid media 4 and the punctiform biological material 5 can be seen within the circle K delimiting a broken cross-sectional view of the container 3.

Generally, the container 3 may be the container of a multi-use bioreactor 1 intended for repeated use, as shown in FIG. 12 by way of example, or else of a single-use bioreactor intended for one-way use, as shown in FIGS. 13 to 18 by way of example.

In the case of a multi-use bioreactor, the container 3 advantageously comprises stainless steel or is made of stainless steel. The device 8 for supporting an image capturing device 9, which will be described in more detail below, may also comprise stainless steel, or at least one or more of its components and for example the main body 10 of the windows 11 disclosed herein and shown in FIG. 7 may comprise or be made of stainless steel.

Any stainless steel may be used for this purpose, especially also austenitic and ferritic stainless steels, but preferably only as far as they remain rust-free when practicing the invention.

The stainless steel may preferably also comprise or may entirely consist of 316L pharmaceutical grade steel.

Furthermore, titanium and Monel alloy with a high copper content may also be used, in principle, and when the material is used for the illumination device, in particular for the housing body thereof, it may also be enameled.

In the case of single-use reactors 1, the container 3 for holding fluid media containing biological material may comprise a plastic, in particular a sterilizable plastic, or may be made of a plastic, in particular a sterilizable plastic. In this case, the container 3 does not have the shape shown in FIG. 12 but may even be in the form of a bag.

Furthermore, more than one port 6 may be provided on the container 3, which is also referred to as a feedthrough 6 in each case.

Preferably, these feedthroughs 6 comprise a standard port, as is the case in particular also in the embodiment shown in FIG. 12, for example an Ingold port, a Broadly James port, a B. Braun safety port, or a port in compliance with a different standard.

In the case of one-way reactors or single-use reactors, the feedthrough 6 may also comprise a tri-clamp port, sanitary clamp port, or a manufacturer-specifically adapted port, as can be seen in FIGS. 13 to 18, by way of example.

The feedthroughs 6 each have a through-opening 7 of a defined diameter, which typically connects the interior of a bioreactor 1 to the exterior thereof or provides access to the container 3.

Figure 5:
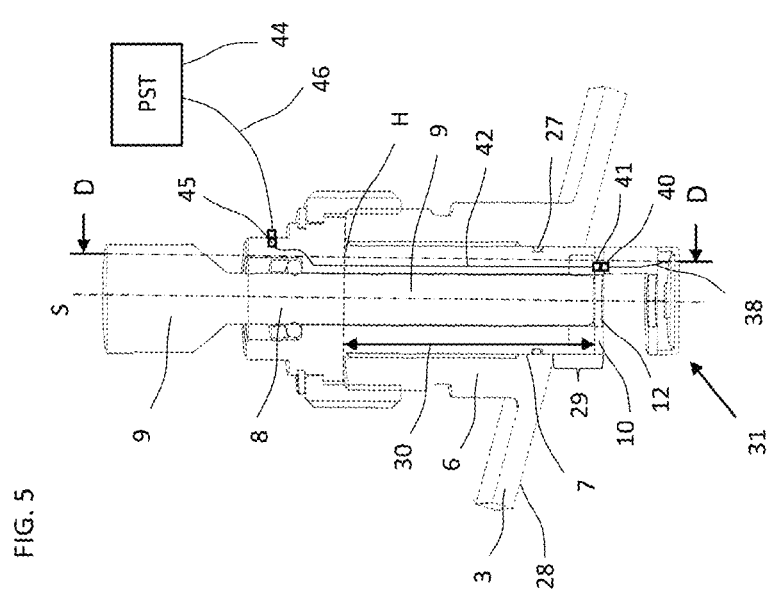
FIG. 5 is another cross-sectional view of the first preferred embodiment of the device for supporting an image capturing device which is arranged in a through-opening of a container for holding fluid media containing biological material, although the container is shown only partially, the view being taken along the sectional plane illustrated as sectional plane A-A in FIG. 4 slightly inclined thereto.

These through-openings 7 of ports 6 can be seen particularly well in FIGS. 1, 5, and 6.

A device 2 for supporting an image capturing device 9, in particular a microscopic device, is arranged in at least one through-opening 7, and the device 2 for supporting an image capturing device 9 is held at least partially in the through-opening 7 of the feedthrough 6, as in the context of the present disclosure it is disclosed hereby that portions of the device 2 may protrude into the interior of the container 3 and may also protrude beyond the through-opening 7 of feedthrough 6 to the exterior of the container 3.

The bioreactor 1 may also have a plurality of feedthroughs 6, and a device 2 for supporting an image capturing device 9 may be arranged in each of those feedthroughs.

In this case, the same type of image capturing device 9 may be arranged in each device 2, or else different embodiments of the image capturing device 9 may be arranged therein.

For example, a first preferred embodiment comprises a microscope probe 8 known per se to a person skilled in the art, which has a substantially cylindrical shape and is supported on the device 2 in a detachable manner, but nevertheless firmly.

The device 2 for supporting an image capturing device 8 will now be described in more detail with reference to FIGS. 1 to 4.

As can be seen particularly well from FIG. 1, the device 2 comprises a holder body 13 which has a cylindrically symmetrical shape, in particular a columnar shape, and is preferably formed in one piece.

The holder body 13 has a preferably cylindrical receiving area 14, in the form of a through-opening, which is sealed fluid-tightly, in particular hermetically, by a window 11, on the side associated with the interior of the bioreactor 1.

Figure 7:
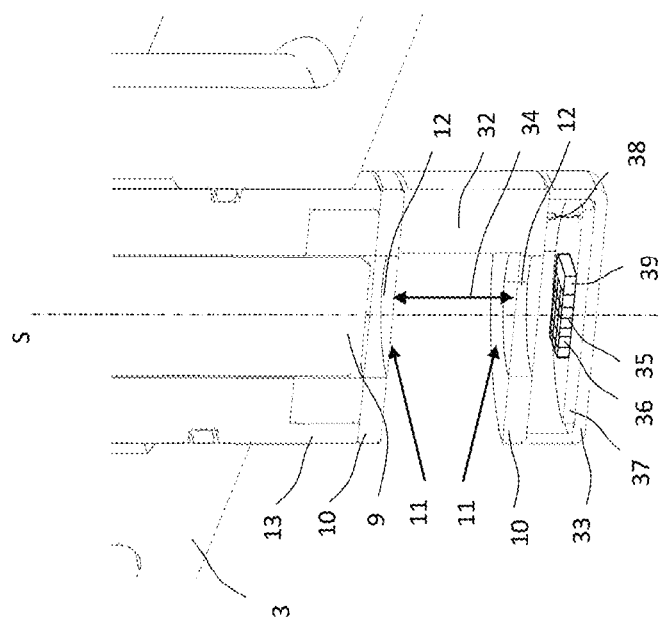
FIG. 7 is a detail view of a lower portion of FIG. 5, but slightly rotated and inclined with respect to the view of FIG. 5.

As can be seen clearly also in FIG. 7, for example, the window 11 comprises a transparent element 12 which is secured in a main body 10 in a fluid-tight, in particular hermetically sealed manner.

The transparent element 12 is transparent to electromagnetic radiation, since it comprises glass or is made of glass, and the glass preferably comprises or is made of quartz glass or borosilicate glass.

The holder body 13 together with the window 11 defines a holder 15 for the image capturing device 9, in which the image capturing device 9 is held in a detachably mounted manner.

For this purpose, the holder body 13 may establish a frictional connection to the image capturing device 9, preferably by means of a frictional element 16, preferably an O-ring, as can be seen in FIG. 6, for example.

Frictional element 16 is held in a cylindrical recess 17 of the holder body 13 by a substantially annular pressure element 18 which exerts a defined adjustable force to the frictional element in the axial direction of the holder body 13.

With the resulting defined deformation of the frictional element 16, the image capturing device 9 can be held within the receiving area 14 with a defined resulting force which reliably ensures the position of the image capturing device 9 while still allowing for rapid manual removal thereof from the receiving area 14 or rapid manual introduction into the receiving area 14.

The annular pressure element 18 is fixed in its position in a defined manner by a snap ring 19. The holder body 13 itself has a radially extending lateral shoulder 20 abutting on an upper flange 21 of the feedthrough 6 in a form-fitting manner.

The holder body 13 is releasably but stationary held on the port 6 by means of a cap nut 22 that has a cylindrical receiving area or through-opening 23 and engages over the radially extending shoulder 20.

For this purpose, the cap nut 22 has a thread 24 and the holder body 13 has a mating thread 25.

The cap nut 22 is captured on the holder body 13 by a snap ring 26 so as to be rotatable but only with little axial play, so it cannot be lost.

The device 2 for supporting an image capturing device can be quickly and safely mounted on the respective port 6 and also detached therefrom by rotating the cap nut 22.

By means of a sealing element 27, for example an O-ring, the holder body 13 is held in the through-opening 7 of the container 3 with a positive and frictional fit so as to seal the through-opening 7 fluid-tightly and preferably hermetically.

The axis of symmetry S of the holder body 13, which can be seen in FIGS. 1 and 5, for example, defines the axial or longitudinal direction here, which is referred to in the context of the present disclosure.

When a device 2 for supporting an image capturing device 9 is placed in the through-opening 7 and preferably fixed therein as described above, the axial distance 29 of the window 11 to the inner surface 28 of the bioreactor 1 is defined by the axial distance 30 of the window 11 to the lateral shoulder 20.

The axial distance of the window 11 to the lateral shoulder 20 is measured starting from the underside of the radially extending lateral shoulder 20, as indicated by an auxiliary line H, to the upper surface of the main body 10 of the window 11, as can be seen in FIG. 5, for example.

Here, the axial distance 29 of the window 11 to the inner surface 28 of the bioreactor 1 is the largest distance between the underside of main body 10 to the inner surface 28 of the bioreactor 1, that is the inner surface 28 of the container 3 of bioreactor 1.

When the holder body 13 is placed in the through-opening 7, in particular when the lateral shoulder 20 abuts against a standard port 6 as shown in FIG. 5, for example, the transparent element 12 of the window 11 is preferably arranged within the bioreactor 1.

A set of holder bodies 13 with different axial distances 30 of the transparent element 12 of the window 11 to the lateral shoulder 20 can permit to place the transparent element 12 of the window within the bioreactor 1 at a selective axial position.

Thus, when using a plurality of devices 2 each featuring a different axial distance 30 between the window 11 and the lateral shoulder 20, it is possible to capture different locations of the bioreactor 1. With this procedure and the use of multiple devices 2, it is thus possible to capture a bioreactor 1 with its internal local processes in a considerably better way.

As can be seen in FIGS. 1 to 4, for example, the device 2 for supporting an image capturing device may comprise an illumination device which is designated by reference numeral 31 as a whole and which can be attached to the holder body 13 permanently or detachably.

This illumination device 31 will be described in more detail below with reference to FIGS. 7, 8, and 9.

The illumination device 31 comprises a base portion 32 with a foot portion 33 held thereon.

The foot portion 33 defines a substantially pot-shaped lower portion and hence a housing, with a further window 11 comprising a further main body 10 and a further transparent element 12 hermetically sealed thereto.

The transparent element 12 of the window 11 of foot portion 33 extends substantially parallel to the transparent element 12 of the window 11 disposed on the holder body.

In the assembled state, the window 11 secured to the holder body 13 faces the window 11 of the foot portion 33 or housing 33.

Thus, in the assembled state, the device 2 for supporting an image capturing device 9 and the illumination device 31 thereof define a chamber within the container 3, which chamber has a defined volume that is open in particular towards at least two sides perpendicular to the axis of symmetry S of the holder body 13.

Preferably, the transparent element 12 of the window 11 of illumination device 31 and the transparent element 12 of the window 11 disposed on the holder body 13 of the device 2 for supporting an image capturing device 9 have a defined spacing from each other, as designated by reference numeral 34 in FIG. 7.

As a result, a defined measuring volume is provided between the two windows 11, 11, which, for example, provides a turbidity chamber, if light is irradiated into it in a defined manner and measurements are taken using a sensor 51, which will be described in more detail further below.

For this purpose, or else for the image capturing and/or recording using a microscope probe 8, the illumination device 31 may preferably include an LED 35 or an array 36 of LEDs 35 arranged in the housing 33 or foot portion 33 of the illumination device 31 and supported on a printed circuit board 37 which has at least one multi-conductor 38 connected thereto.

For the sake of clarity, only one of the LEDs 35 within the array 36 of LEDs is designated by a reference numeral, however, the use of a single LED 35 is also within the scope of the present disclosure.

Additionally, a controller 39 is provided on the printed circuit board 37 and is connected thereto by the multi-conductor 38.

The illumination device 31 has at least one electrical connector 40 at the housing thereof, which is connected to the multi-conductor 38.

Figure 8:
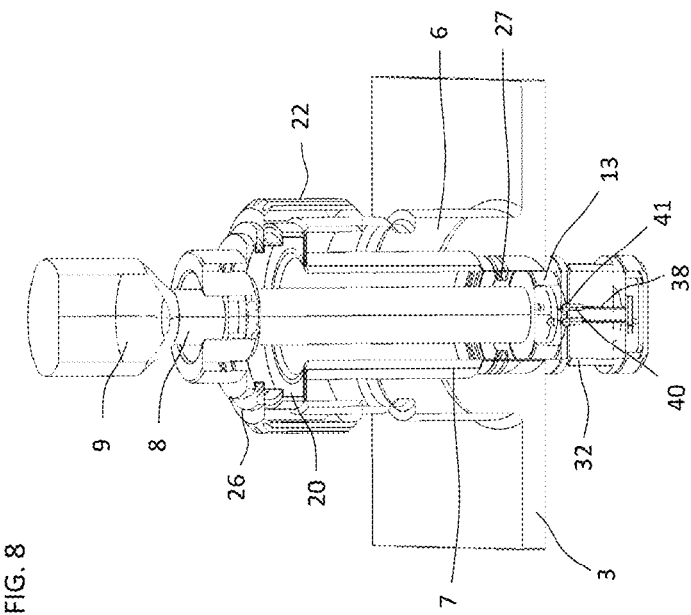
FIG. 8 is a perspective sectional view taken along the sectional plane D-D indicated in FIG. 5 of the first preferred embodiment of a device for supporting an image capturing device which is arranged in a through-opening of a container for holding fluid media containing biological material, although the container is shown only partially, the device being illustrated transparently so that only the outline edges thereof are shown.
Figure 9:
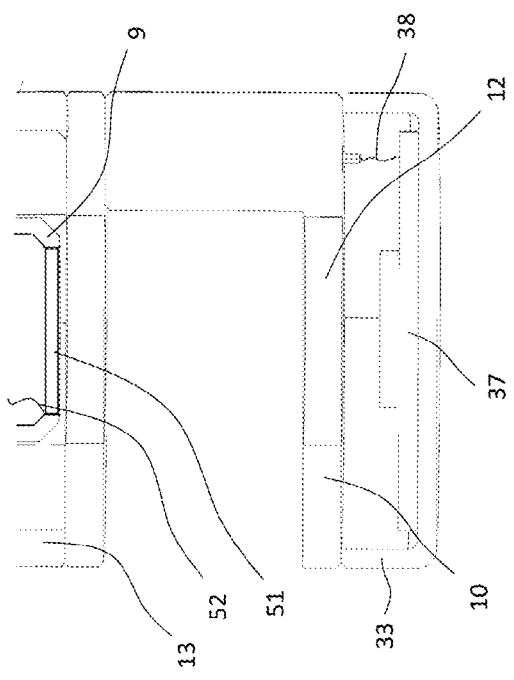
FIG. 9 is a detail view of a lower portion of FIG. 8.

The device 2 for supporting an image capturing device 9 also has at least one electrical connector 41 on the holder body 13 thereof, as can be seen in FIGS. 8 and 9, for example, which is connected to an external control device by the multi-conductor 42.

Electrical connectors 40, 41 are complementary interengagable and are each hermetically sealed.

In the plug-in version of the electrical connectors 40, 41 shown in the figures, the housing of the electrical connector 40, 41 is sealed by an elastomeric component, in connector 40 with respect to the foot portion 33, and in connector 41 with respect to the holder body 13, as shown in FIG. 9 for the connector 41. Materials that can be used here as an elastomeric component include EPDM, NBR, FKM.

The multi-conductors 38, 42 may include signal lines of a communication bus as well as respective power supply lines, in particular for the controller 39 and the LEDs 35.

A preferred communication bus includes, for example, data exchange via OPC XML and includes JAVA programmable clients. Such a communication bus with its clients is described, for example, in "SIMOTION—Description and example for the data exchange via OPC XML interface", Version 1.0 Edition 07/2007, published by Siemens AG.

Alternatively or additionally, the multi-conductors 38, 42 may also carry analog signals, and the LEDs 35 of the array 36 may be controlled directly by an associated, preferably external electronic device, in particular controlled stroboscopically. The process control device (PST) 44 is only shown schematically in FIG. 5, however, it should be appreciated that the process control device 44 is connected to the multi-conductor 42 via yet another multi-conductor 46 by further connectors which are exemplified by the connector 45.

As can be seen from FIG. 5, the holder body 13 is appropriately equipped with this further connector 45 at its upper portion, to which the multi-conductor 42 is connected.

For internal guidance of the multi-conductors 38, 42, and 49, respective through-bores or respective blind holes may be provided in the holder body 13, the base portion 32 and the respective main body 10 of a window 11, for receiving this or these multi-conductor(s), and the attachment thereof will be apparent for a person skilled in the art but is not illustrated in the figures merely for the sake of clarity.

Figure 11:
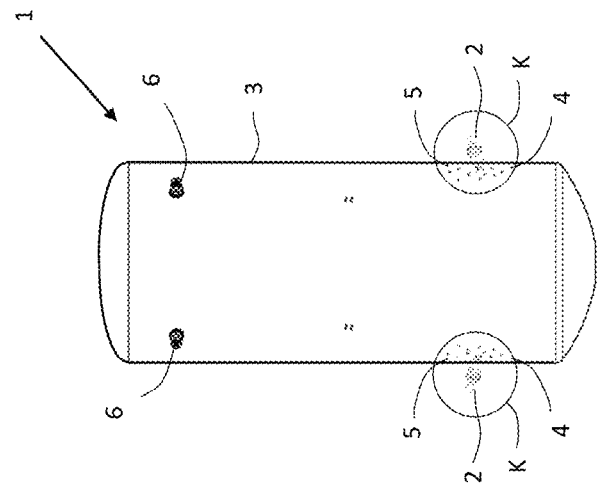
FIG. 11 is a view similar to that of FIG. 5, but illustrating yet another embodiment in which an inductive coupler is arranged in a holder body of the device for supporting an image capturing device and an inductive coupler is arranged in an illumination device of the device for supporting an image capturing device, showing a lower portion thereof.
Figure 15:
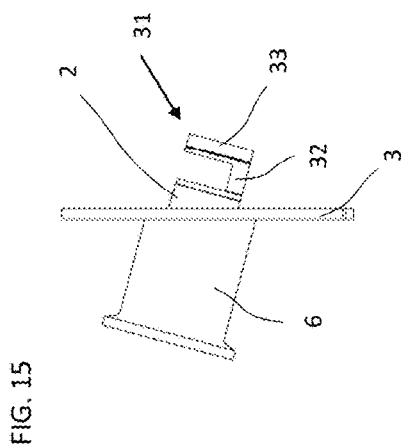
FIG. 15 is a cross-sectional view of the further preferred embodiment of the device for supporting an image capturing device which is arranged in a through-opening of a container for holding fluid media containing biological material, although the container is shown only partially, the view being taken along a sectional plane illustrated as sectional plane F-F in FIG. 14.
Figure 18:
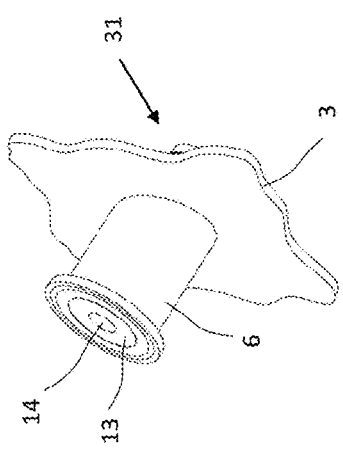
FIG. 18 is a further view of the further preferred embodiment of the device for supporting an image capturing device which is arranged in a through-opening of a container for holding fluid media containing biological material, although the container is shown only partially, the view being taken obliquely from below, as seen from the outside of the container for holding fluid media.
Figure 14:
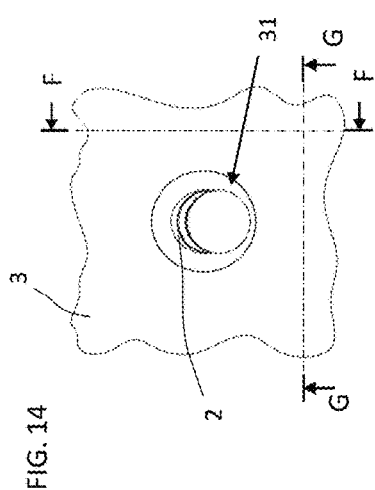
FIG. 14 is a perspective view obliquely from above, but as seen from the interior of a container for holding fluid media, of the further preferred embodiment of the device for supporting an image capturing device which is arranged in a through-opening of the container for holding fluid media containing biological material, although the container is shown only partially.
Figure 17:
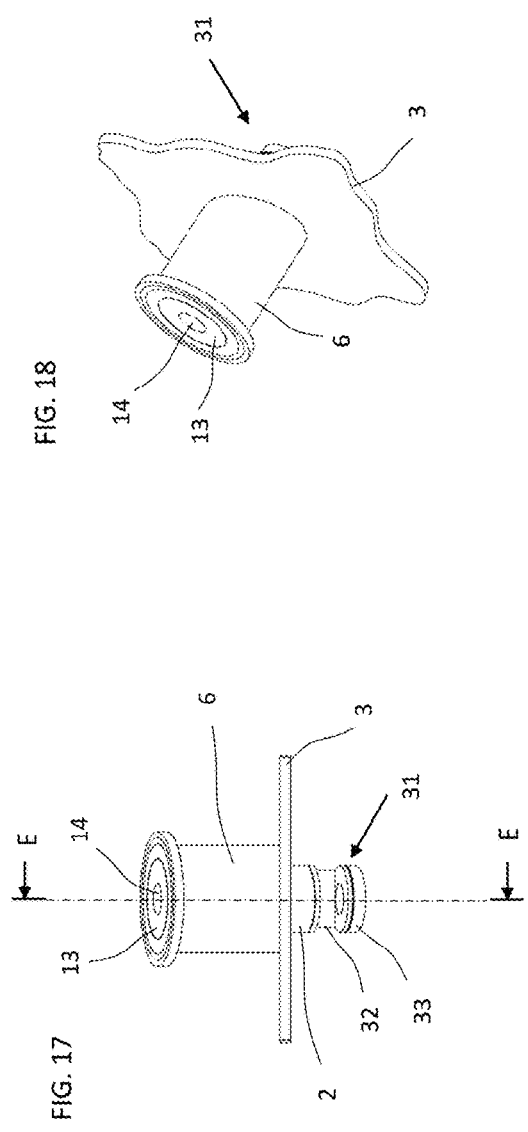
FIG. 17 is a cross-sectional view of the further preferred embodiment of the device for supporting an image capturing device which is arranged in a through-opening of a container for holding fluid media containing biological material, although the container is shown only partially, the view being taken along a sectional plane illustrated as sectional plane G-G in FIG. 14.
Figure 13:
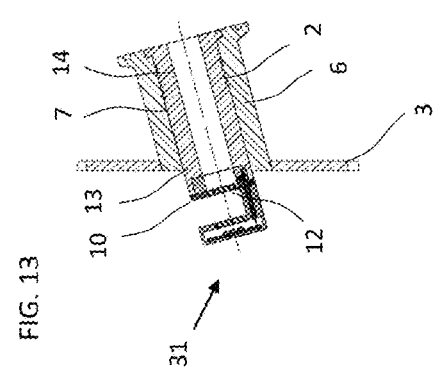
FIG. 13 is a cross-sectional view of a further preferred embodiment of a device for supporting an image capturing device which is arranged in a through-opening of a container for holding fluid media containing biological material, although the container is shown only partially, the view being taken along a sectional plane illustrated as sectional plane E-E in FIG. 17, and the bioreactor being a single-use bioreactor.
Figure 16:
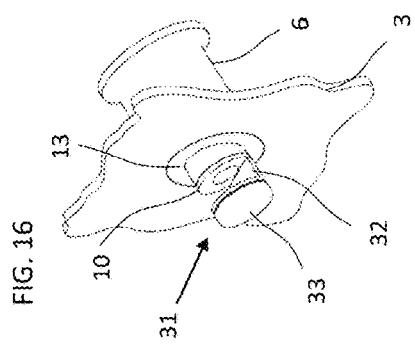
FIG. 16 is another perspective view obliquely from above, but as seen from the interior of a container for holding fluid media, of the further preferred embodiment of the device for supporting an image capturing device which is arranged in a through-opening of the container for holding fluid media containing biological material, although the container is shown only partially.

Furthermore, as shown by way of example in FIG. 11, the device 2 for supporting an image capturing device 9 may have at least one inductive coupler 47 on its holder body 13, and the illumination device 2 may have at least one inductive coupler 48 on its housing 33 or foot portion 33, and these couplers can be coupled inductively with each other in their mounted state and are each hermetically sealed against the one or more fluid media 4.

These couplers 47, 48 permit to supply electrical power both for the controller 39 and for the LEDs 35 of the array of LEDs from the holder body 13 and feed it into an electrical storage device of the controller 39 in a sufficient quantity for the processes described herein.

For this purpose, the inductive coupler 47 may be connected to the further connector 45 via a multi-conductor 49, and the inductive coupler 48 may be connected to the controller 39 via a further multi-conductor 50.

Furthermore, the couplers 47, 48 allow for bidirectional transfer of time- or frequency-modulated signals, so that appropriate control by the process control device 44 can be performed in this embodiment as well.

In order to be able to transmit both electrical power and the time- or frequency-modulated signals without interference, the inductive couplers 47, 48 each comprise a coil with one or more turn(s), of which, however, only a single turn is shown in FIG. 11 by way of example.

Furthermore, it is also possible for the LEDs 35 of the illumination device to emit only individual light pulses under defined control, in particular under control of the associated electronic device, in the present case the process control device (PSI) 44. During the emission of each one of the light pulses or pulses of electromagnetic radiation emitted during the stroboscopic illumination, a microscope probe 8 including an image capturing device may capture a respective image, in synchronism with such pulses, for example, whereby blurring as caused by the movement of the fluid medium 4 or the fluid media 4 and the biological material 5, for example, can be significantly reduced in the image recording.

Figure 10:
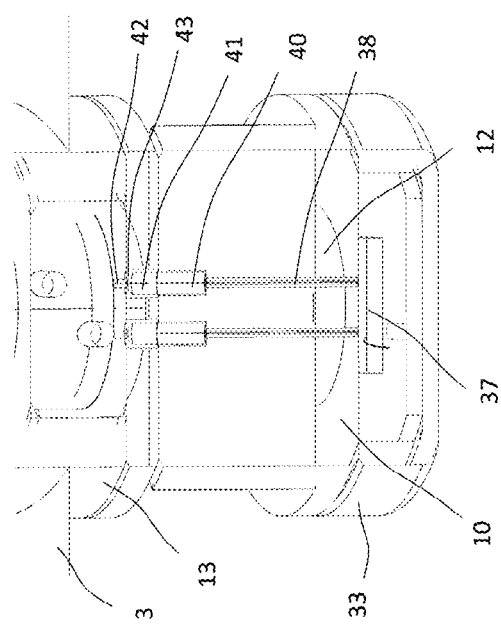
FIG. 10 is a view similar to that of FIG. 5, but illustrating a further embodiment in which a sensor for detecting electromagnetic radiation is arranged in the device for supporting an image capturing device, showing a lower portion thereof.

A further preferred embodiment is shown in FIG. 10, in which the image capturing device 9 comprises an sensor 51 for measuring the wavelength and/or intensity of electromagnetic radiation, instead of the microscope probe 8 or integrated into the latter.

The sensor 51 for measuring the wavelength and/or intensity of electromagnetic radiation can be used, first, to measure the intensity and/or wavelength of the radiation emitted by the LEDs 35. Since the LEDs undergo an aging process and/or their emission spectrum may depend on the ambient temperature, for example, their emission is controllable in the operating state using the sensor 51. However, the at least one sensor 51 can also be used to control and/or characterize the condition of the biological material 5 within the bioreactor 1. For example, the wavelength of the electromagnetic radiation received by the sensor can provide information about the biological material 5, through scattering or backscattering of the biological material 5 illuminated in the operating state. If, for example, the biological material 5 such as specific algae, is illuminated with white light, in particular for their growth, they will scatter back green light, for example. The intensity of the green light may depend on the concentration of the algae and/or their growth state. This information can be used to control the processes within the bioreactor 1, such as nutrient supply, temperature, and the like. Obviously, it is also possible to measure fluorescence and further optical properties.

FIG. 10 shows the sensor 51 as an independent component, and in this case the image capturing device 9 practically comprises only one pixel in the sense of the present disclosure.

If, however, the device 2 for supporting an image capturing device 9 has at least one sensor, in particular an image capturing device within a microscope probe 8 or associated with this microscope probe 8, and if in the operating state this image capturing device is used to capture the radiation intensity and/or wavelength of the electromagnetic radiation in the interior of the bioreactor 1, in particular in the interior of container 3, it is possible to measure the radiation intensity and/or the wavelength in a spatially resolved manner. Furthermore, for measuring the wavelength, coatings on the transparent element 12 will be described below, by way of example. Moreover, both optical and electronic type filters disposed within a microscope probe 8 can be used for this purpose in the image capturing device, for example.

With such a sensor 51 it is also possible, for example, to perform a turbidity measurement, by having this sensor 51 capturing the electromagnetic radiation that emerges through the window 11 of the illumination device 31 after having passed through the window 11 secured to the holder device or holder body 13. Such a measurement may also be performed under the control of the process control device (PST) 44, and for this purpose the sensor 51 is connected to the process control device (PST) 44 by a multi-conductor 52, for example similar to what is shown in FIG. 5 for the controller 39.

Process control with the use of an in-situ microscope makes it possible here to acquire quantitative and morphological information about the respective cells of the biological material 5. An optimization of the influencing parameters for an optimized or at least improved yield is directly derived therefrom. Such parameter include, for example, the fumigation rate, the fumigation composition, temperature, pH, rX, concentrations of dissolved gases, mixing/stirrer speed, feed rate, feed composition, cultivation time, activating or inhibiting factors, and may also include further influencing factors.

In the present preferred embodiments, a window 11 or both windows 11 each provide a glass seal for a transparent element 12, preferably a GTMS compression glass seal, as will be described below with reference to FIG. 19.

FIG. 19 shows a schematic sectional view along an axis of symmetry Sofa window 11 described herein for explaining the method for producing such a window.

The window 11 shown in FIG. 19 comprises an annular or cylindrical main body 10 made of steel, which encloses the transparent element 12 laterally while exerting thereon a compressive force which ensures a permanently hermetic connection between the transparent element 12 and the main body 10 sufficiently pressure-resistant and heat-resistant for the purposes of the present invention.

For producing such a window, the transparent element comprising glass or made of glass is accordingly arranged within the main body 10, preferably in approximately its final shape, and is heated together with the main body until the glass of the transparent element 12 has exceeded its glass transition temperature $T_g$ or hemisphere temperature and begins to fuse to the main body 10.

Once fused, the assembly of transparent element 12 and main body 10 is then cooled to room temperature, thereby forming a respective window 11 that includes a substantially sheet-like transparent element 12.

Since the stainless steel of the main body 10 has a thermal expansion coefficient that is greater than that of the glass of the transparent element 12, it will exert a compressive stress to the glass of the transparent element 12 as soon as the glass of the transparent element begins to solidify, which compressive stress is increasing with decreasing temperature.

Once the cooling has been completed, the main body 10 will then permanently and reliably hold the transparent element 12 in a hermetically sealed and temperature-stable manner due to this quasi-frozen compressive stress.

Such a compression glass seal is also referred to as a Glass-To-Metal Seal (GTMS) or GTMS compression glass seal in the present disclosure.

In such a glass-to-metal joint, the metal exerts pressure forces on the glass over the entire operating temperature range, in particular even at temperatures up to at least 121° C., preferably even up to 141° C., which pressure forces cause a compressive stress between the metal and the glass and help to ensure that the glass-to-metal joint remains permanently and reliably fluid-tight as well as hermetically sealed.

Furthermore, no gaps will arise with such glass-to-metal joints. By contrast, if conventional sealing means such as O-rings are used, gaps may arise and may provide room for contamination that is often difficult to remove.

For this purpose, a difference in the coefficients of thermal expansion is advantageous, which reliably maintains the compressive stress between the glass of the transparent element 12 and the metal of the annular or cylindrical main body 10 of the window 11 at least over the range of operating temperatures.

This difference between the expansion coefficient $CTE_M$ of the metal and the expansion coefficient $CTE_G$ of the glass of the transparent element 12 may be less than $80 \times 10^{-6}$/K, for example, preferably less than $30 \times 10^{-6}$/K, or most preferably less than $20 \times 10^{-6}$/K. Here, the coefficient of thermal expansion of the metal $CTE_M$ should be greater than the coefficient of thermal expansion of the glass $CTE_G$ in each case. In any cases, however, this difference should preferably be at least $1 \times 10^{-6}$/K.

For example, quartz glass has a $CTE_{G\ of}$ $0.6 \times 10^{-6}$/K and can be combined, for example, with stainless steels having a $CTE_M$ of 17 to $18 \times 10^{-6}$/K.

The bioreactor 1 and the device 2 for supporting an image capturing device are each autoclavable individually, or else the bioreactor 1 and the device 2 for supporting an image capturing device are also autoclavable together. This means that in particular the device for supporting an image capturing device including its windows 11 as disclosed herein is hermetically sealed so as to withstand a treatment with saturated steam at a temperature of 121° C., in particular also 141° C., so that ingress of saturated steam or fluids generated thereby into the device 2 is prevented.

In the context of the present disclosure, autoclavable is understood to mean autoclavable in the sense of DIN EN ISO 14937; EN ISO 17665, which applies to medical devices.

Surprisingly, it has been found that 3500 autoclaving cycles at 2 bar and 134° C. were possible with the devices for supporting an image capturing device as disclosed herein.

This also allows for the advantageous steaming-in-place (SIP) which will be known to a person skilled in the art.

In this permanent hermetical and heat-stable sealing state, the glass of the transparent element 12, can either be used directly, preferably after verifying the respective face or main surface 53, 54, or may be subjected to further surface processing procedures such as polishing or shaping grinding.

In this way, the respective transparent element 12 may have plane-parallel faces or main surfaces 53 and 54, or else the transparent element 12 may be shaped to become one of plano-convex, plano-concave, biconvex, biconcave, convexo-concave, or concavo-convex, as can be seen in the sectional views of FIGS. 20 to 26.

In the case of lower optical requirements on the surface quality, in particular for the beam paths used for the measurement with the embodiment described with reference to FIG. 10, the transparent element 12 may also be held in a corresponding negative mold which substantially already corresponds to the final shape thereof, during the fabrication process.

The main surfaces 53, 54 may have a wavelength-selective coating which provides an optical bandpass or edge filter. With such an optical filter, predefined wavelengths may be irradiated into the container 3 by the illumination device 31, and identical wavelengths or different wavelengths may be measured, in particular captured by the sensor 51. This coating may be provided only on one or else on both main surfaces 53, 54.

Without such a coating, in particular without any coating, the transparent element 12 of at least one window 11 exhibits a transmittance of greater than 80%, most preferably greater than 90%, in a spectral range of wavelengths between 250 and 2000 nm.

Figure 28:
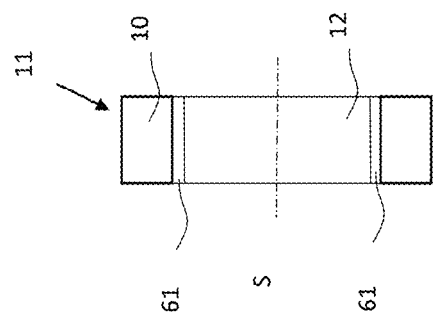
FIG. 28 is a schematic sectional view along an axis of symmetry S of a window described herein, in which the transparent element comprises quartz glass, for explaining the method of producing such window.
Figure 29:
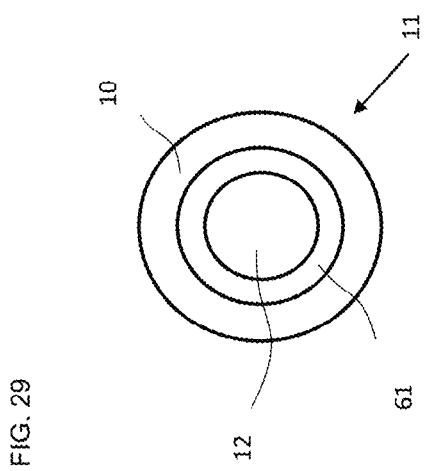
FIG. 29 is a top plan view of the window shown in FIG. 28, in which the transparent element comprises quartz glass.

If the transparent element 12 of the window 11 consists of quartz glass or is made of quartz glass, as shown in FIGS. 28 and 29, for example, it is also possible, instead of a laser welding seam, to use a further glass 61 or glass solder 61, in particular lead-free glass 61 or glass solder 61 to hermetically seal the quartz glass to the annular or cylindrical main body 10 of the window 11, in particular fluid-tightly and hermetically.

The main body 10 of the window 11 is preferably joined directly to the holder body 13 and/or the housing 33 of the illumination device 31, in a hermetically sealed manner in each case, in particular by laser welding, so that the housing 33 is hermetically sealed thereby and the holder body 13 is also hermetically sealed at its lower end against the interior of the container 3.

The laser welding seam formed thereby is only indicated in FIG. 22 by way of example, by reference numeral 55.

If, now, light is emitted by one of the LEDs 35, this light is transmitted through the respective window 11 arranged in front of this LED 35 and causes a predefined illumination of the volume located between the two windows 11.

Figure 27:
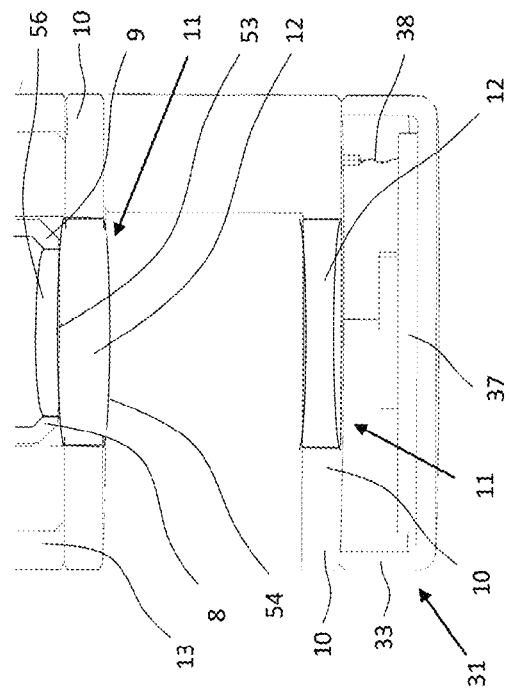
FIG. 27 is a detail view similar to that of FIG. 5, but illustrating a further embodiment in which a window forms part of a microscopic device associated therewith, in particular of a microscope probe.

A further preferred embodiment is resulting if the window as shown in FIG. 21, for example, is used together with a microscope probe 8, as can be seen in FIG. 27, for example, and if this window 11 forms part of the microscopic device associated therewith, namely the microscope probe 8. In this case, the lower main surface 54 alone or both main surfaces 54, 53 may have a beam- or wave-forming effect, for example, so that it is possible, in principle, to achieve higher numerical apertures for the imaging beam path, since a larger effective angular range for the incoming electromagnetic radiation can be provided for the first optical lens element 56 of the microscope probe 8.

As a result, not only the resolution of the microscope probe 8 can be increased, but furthermore the total available intensity of the electromagnetic radiation can be increased, so that, when this window as shown in FIG. 21 is used in particular also for the embodiment shown in FIG. 10, an enhanced signal-to-noise ratio is resulting for the measurement obtained thereby and is converted into electrical signals, for example.

The emission of electromagnetic radiation of the LEDs 35 may also be influenced similarly, for example by using the window shown in FIG. 22 for the housing 33 of the illumination device 31, thereby achieving illumination with an overall larger opening angle.

Alternatively, the holder body 13 may also comprise or be made of a high temperature resistant plastic, in particular a thermoplastic material such as polyaryletherketone, in particular polyetheretherketone, PEEK.

If the holder body 13 comprises or is made of a high temperature resistant plastic, in particular a thermoplastic material such as polyaryletherketone, in particular polyetheretherketone, PEEK, this holder body 13 need not necessarily have to be completely hermetic as described in the context of the present disclosure, but nevertheless it will be possible to achieve quite valuable operating and application times.

For example, the holder body 13 which comprises PEEK or is made of PEEK may have a preferably columnar receiving area or through-opening of circular cross-sectional shape, and a transparent element 12 which also has a circular outer lateral contour may have an outer diameter that is larger than the inner diameter of the circular receiving area or through-opening of the holder body 13 by about 1/10. When the holder body 13 is heated to a temperature of about 200° C., the transparent element 12 can then be inserted into this receiving area or through-opening, and when being cooled down, a compressive stress is resulting as described above, for example of about 38 MPa, which is still well below the yield strength of PEEK of 110 MPa.

In the embodiments disclosed herein, the illumination device may be held firmly on the holder body 13, in particular by welding the base part 32 to the holder body 13, or may alternatively be held so as to be detachable. For detachably mounting the illumination device 31 to the holder body 13, fastening means may be provided which comprise dowel pins, for example, which can engage in associated fitting grooves or precisely fitting blind holes of the respective second housing.

By way of example, FIG. 11 only shows the dowel pin 57, 58 of the holder body 13 engaging into a respective associated bore 59, 60 of the base portion 32.

The invention generally relates to a device for supporting an image capturing device on a bioreactor, to a bioreactor comprising a device for supporting an image capturing device, and to a method for propagation or cultivation of biological material which uses a device for supporting an image capturing device, in particular a microscopic device, which comprises a window including a transparent element that is transparent to electromagnetic radiation, and a holder for the image capturing device, wherein the device for supporting an image capturing device is held at least partially in a through-opening of a feedthrough of a container for holding fluid media containing biological material, wherein the window preferably seals the through-opening.

LIST OF REFERENCE NUMERALS:

| | |
|---|---|
| 1 | Bioreactor |
| 2 | Supporting device |
| 3 | Container |
| 4 | Fluid medium or fluid media |
| 5 | Biological material |
| 6 | Port or feedthrough |
| 7 | Through-opening of container 3 |
| 8 | Microscope probe |
| 9 | Image capturing device |
| 10 | Main body |
| 11 | Window |
| 12 | Transparent element |
| 13 | Holder body |
| 14 | Receiving area or through-opening |
| 15 | Holder |
| 16 | Frictional element |
| 17 | Cylindrical recess |
| 18 | Annular pressure element |
| 19 | Snap ring |
| 20 | Radially extending lateral shoulder |
| 21 | Upper flange |
| 22 | Cap nut |
| 23 | Receiving area or through-opening |
| 24 | Thread |
| 25 | Mating thread |
| 26 | Snap ring |
| 27 | Sealing element |
| 28 | Inner surface |
| 29 | Axial distance |
| 30 | Axial distance |
| 31 | Illumination device |
| 32 | Base portion |
| 33 | Foot portion or housing |
| 34 | Spacing |
| 35 | LED |
| 36 | Array of LEDs |
| 37 | Printed circuit board |
| 38 | Multi-conductor |
| 39 | Controller |
| 40, 41 | Electrical connector |
| 42 | Multi-conductor |
| 43 | Elastomer component |
| 44 | Process control device (PST) |
| 45 | Further connector |
| 46 | Multi-conductor |
| 47, 48 | Inductive coupler |
| 49, 50 | Multi-conductor |
| 51 | Sensor |
| 52 | Multi-conductor |
| 53, 54 | Main surface |
| 55 | Laser welding seam |
| 56 | Optical lens element |
| 57, 58 | Dowel pin |
| 59, 60 | Fitting grooves or blind holes |
| 61 | Further glass or glass solder |
| S | Axis of symmetry |
| H | Auxiliary line |

What is claimed is:

1. A device for supporting an image capturing device in a feedthrough of a bioreactor, comprising:
a window including a transparent element, the transparent element is transparent to electromagnetic radiation; and
a holder for the image capturing device, wherein the holder comprises a holder body made of a high temperature resistant plastic selected from the group consisting of a thermoplastic material, polyaryletherketone, and polyetheretherketone,
wherein the holder body has a columnar receiving area or through-opening of circular cross-sectional shape,
wherein the transparent element has a circular outer lateral contour and an outer diameter that is larger than the inner diameter of the circular receiving area or through-opening of the holder body by about 10%,
wherein the transparent element is inserted into the receiving area or through-opening of the holder body when the holder body is heated to a temperature of about 200° C., and wherein when being cooled down, results in a compressive stress on the transparent element,
wherein the holder body has a portion that is sized and configured to pass into an interior of the bioreactor from an exterior of the bioreactor through the feedthrough, and
wherein the transparent element of the window has a shape selected from a group consisting of sheet, plano-convex, plano-concave, biconvex, biconcave, convexo-concave, and concavo-convex.

2. The device of claim 1, wherein the holder has a cylindrically symmetrical shape and has a receiving area, the window hermetically sealing the receiving area on a side associated with the interior of the bioreactor.

3. The device of claim 1, wherein the transparent element exhibits a transmittance of greater than 80% in a spectral range of wavelengths between 250 and 2000 nm.

4. The device of claim 1, wherein the transparent element of the window comprises a material selected from a group consisting of glass, quartz glass, and borosilicate glass.

5. The device of claim 1, wherein the transparent element forms part of a microscopic device.

6. The device of claim 1, wherein the holder has a radially extending lateral shoulder, the lateral shoulder being positioned a first axial distance from the transparent element so that the first axial distance defines a second axial distance between the transparent element and the inner surface of the bioreactor.

7. The device of claim 6, further comprising an illumination device disposed on the holder at a side of the holder configured to be in the inner surface of the bioreactor.

8. The device of claim 1, further comprising an illumination device, the illumination device having a housing and a second window including a second transparent element.

9. The device of claim 8, wherein the second transparent element is secured to the housing by a compression glass seal or welding.

10. The device of claim 8, wherein the transparent element and the second transparent element have a predefined spacing from each other.

11. The device of claim 8, further comprising a first electrical connector on the holder and a second electrical connector the housing, wherein the first and second electrical connectors are each hermetically sealed and complementary interengagable.

12. The device of claim 8, further comprising a first inductive coupler on the holder and a second inductive coupler on the housing, wherein the first and second inductive couplers are each hermetically sealed and adapted to be coupled inductively.

13. The device of claim 8, wherein the illumination device comprises an LED or an array of LEDs arranged in the housing.

14. The device of claim 13, further comprising an associated electronic device configured to control the LED or array of LED's stroboscopically.

15. The device of claim 8, wherein the illumination device is autoclavable.

16. The device of claim 1, wherein the window is sized and configured to pass into the interior of the bioreactor from the exterior of the bioreactor through the feedthrough.

17. A device for supporting an image capturing device in a feedthrough of a bioreactor, comprising:
  a window including a transparent element, the transparent element is transparent to electromagnetic radiation; and
  a holder for the image capturing device, wherein the holder comprises a holder body made of a high temperature resistant plastic selected from the group consisting of a thermoplastic material, polyaryletherketone and polyetheretherketone,
 wherein the holder body has a columnar receiving area or through-opening of circular cross-sectional shape, wherein the transparent element has a circular outer lateral contour and an outer diameter that is larger than the inner diameter of the circular receiving area or through-opening of the holder body by about 10%, wherein the transparent element is inserted into the receiving area or through-opening of the holder body when the holder body is heated to a temperature of about 200° C., and wherein when being cooled down results in a compressive stress on the transparent element,
 wherein the holder body has a portion that is sized and configured to pass into an interior of the bioreactor from an exterior of the bioreactor through the feedthrough, and
 wherein the transparent element of the window has a shape selected from a group consisting of plano-convex, plano-concave, biconvex, biconcave, convexo-concave, and concavo-convex.

* * * * *